United States Patent
Finger et al.

(10) Patent No.: US 6,358,204 B1
(45) Date of Patent: Mar. 19, 2002

(54) ULTRASONIC SYSTEM AND METHOD FOR STORING DATA

(75) Inventors: David J. Finger, San Jose; Ismayil M. Guracar, Redwood City; D. Grant Fash, III, Saratoga; Shahrokh Shakouri, San Jose, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/354,257

(22) Filed: Jul. 15, 1999

Related U.S. Application Data

(62) Division of application No. 09/001,489, filed on Dec. 31, 1997, now Pat. No. 6,171,244.

(51) Int. Cl.[7] .............................................. A61B 08/00
(52) U.S. Cl. ........................ 600/437; 600/443; 600/447
(58) Field of Search ................................ 600/443, 444, 600/447, 448, 449, 437

(56) References Cited

U.S. PATENT DOCUMENTS

| | | |
|---|---|---|
| 4,271,842 A | 6/1981 | Specht et al. |
| 4,662,222 A | 5/1987 | Johnson |
| 4,694,680 A | 9/1987 | Takeuchi et al. |
| 5,156,152 A | 10/1992 | Yamazaki et al. |
| 5,168,877 A | 12/1992 | Yamaguchi et al. |
| 5,322,066 A | 6/1994 | Miyataka et al. |
| 5,396,890 A | 3/1995 | Weng |
| 5,409,007 A | 4/1995 | Saunders et al. |
| 5,461,921 A | 10/1995 | Papadakis et al. |
| 5,474,073 A | 12/1995 | Schwartz et al. |

(List continued on next page.)

FOREIGN PATENT DOCUMENTS

EP   0 829 735 A2   3/1998

OTHER PUBLICATIONS

Stytz, M. R., Frieder, G. Frieder, O., "Three–Dimensional Medical Imaging: Algorithms and Computer Systems", ACM Computing Surveys, vol. 23, No. 4, Dec. 1991, pp. 421–499.

Basoglu et al., "A Programmable Ultrasound Subsystem for Native Image Processing"; SPIE vol. 2707; pp. 378–388 (1996).

Apollo VP3; VIA WWW page printout; Nov. 10, 1997.

Acclerated Graphics Port; AGP tutorial and AGP benefits; WWW page print out; Nov. 14, 1997.

Intel 440LX; AGP set and product brief; Intel WWW page print out; Nov. 4, 1997.

*Primary Examiner*—Marvin M. Lateef
*Assistant Examiner*—Maulin Patel
(74) *Attorney, Agent, or Firm*—Craig A. Summerfield; Brinks Hofer Gilson & Lione

(57) ABSTRACT

An apparatus and method for processing ultrasound data is provided. The apparatus includes an interface operatively connected to a memory, a programmable single instruction multiple data processor (or two symmetric processors), a source of acoustic data (such as a data bus) and a system bus. The memory stores data from the processor, ultrasound data from the source, and data from the system bus. The processor has direct access to the memory. Alternatively, the system bus has direct access to the memory. The interface device translates logically addressed ultrasound data to physically addressed ultrasound data for storage in a memory. The translation is the same for data from both the processor and the source for at least a portion of a range of addresses. The memory stores both ultrasound data and various of: beamformer control data, instruction data for the processor, display text plane information, control plane data, and a table of memory addresses. One peripheral connects to the ultrasound apparatus. An interface adapter, powered from the ultrasound apparatus, translates information transferred between the peripheral and the ultrasound apparatus. The adapter connects non-standard peripherals to various standard interfaces on the ultrasound apparatus.

55 Claims, 8 Drawing Sheets

U.S. PATENT DOCUMENTS

| | | |
|---|---|---|
| 5,477,858 A | 12/1995 | Norris et al. |
| 5,483,963 A | 1/1996 | Butler et al. |
| 5,485,842 A | 1/1996 | Quistgaard |
| 5,492,125 A * | 2/1996 | Kim et al. .................. 600/443 |
| 5,524,629 A | 6/1996 | Mahony |
| 5,529,068 A | 6/1996 | Hoenninger, III et al. |
| 5,549,111 A * | 8/1996 | Wright et al. ............... 600/447 |
| 5,588,032 A | 12/1996 | Johnson et al. |
| 5,630,421 A | 5/1997 | Barlow et al. |
| 5,645,066 A | 7/1997 | Gandini et al.. |
| 5,673,407 A | 9/1997 | Poland et al. |
| 5,709,206 A | 1/1998 | Teboul |
| 5,709,209 A | 1/1998 | Friemel et al. |
| 5,715,823 A | 2/1998 | Wood et al. |
| 5,739,691 A | 4/1998 | Hoenninger, III |
| 5,765,010 A | 6/1998 | Chung et al. |
| 5,779,641 A | 7/1998 | Hatfield et al. |
| 5,787,889 A | 8/1998 | Edwards et al. |
| 5,795,296 A | 8/1998 | Pathak et al. |
| 5,795,297 A | 8/1998 | Daigle |
| 5,810,747 A | 9/1998 | Brudny et al. |
| 5,853,367 A | 12/1998 | Chalet et al. |
| 5,911,051 A | 6/1999 | Carson et al. |
| 5,964,708 A | 10/1999 | Freeman et al. |
| 5,987,587 A | 11/1999 | Meltzer |

* cited by examiner

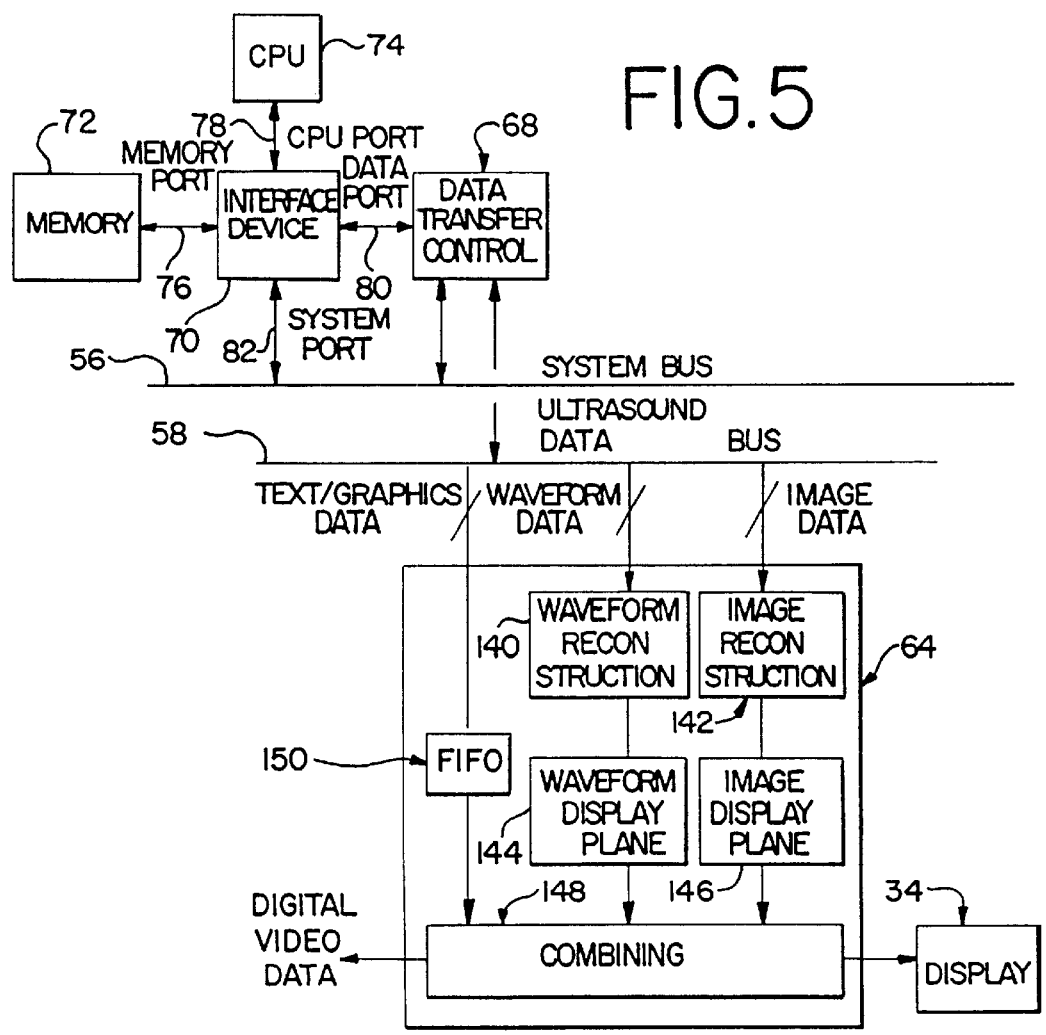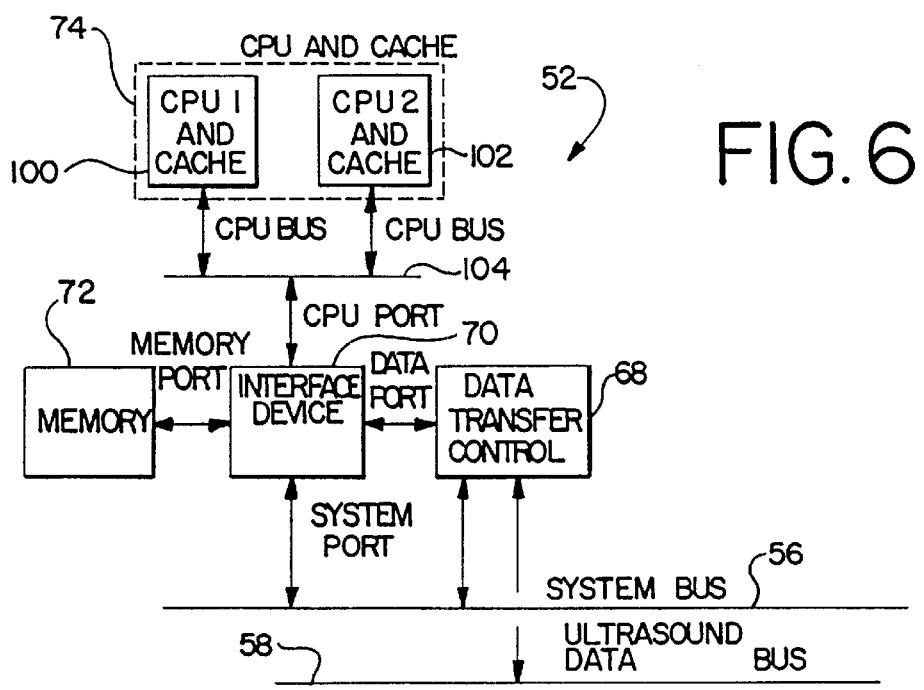

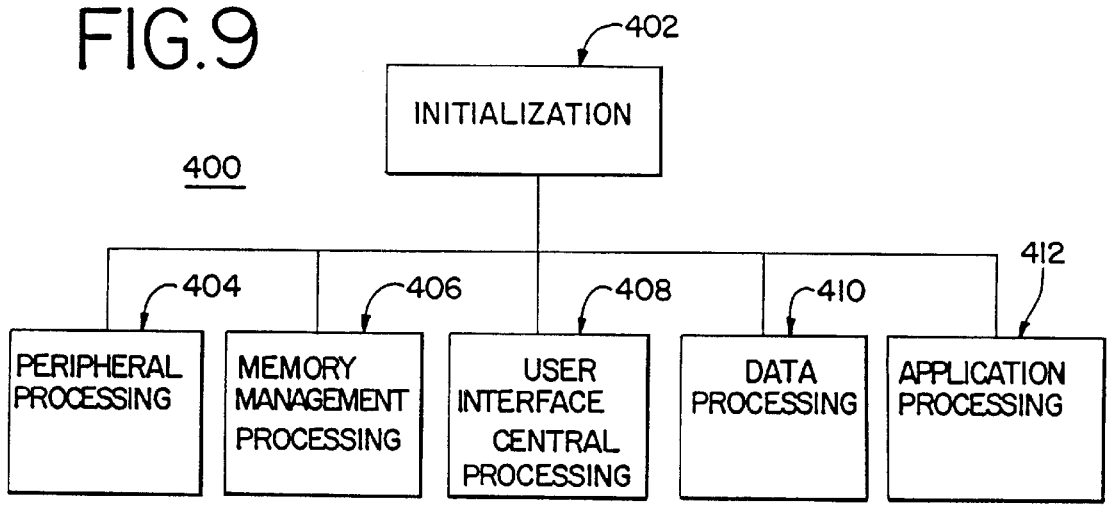
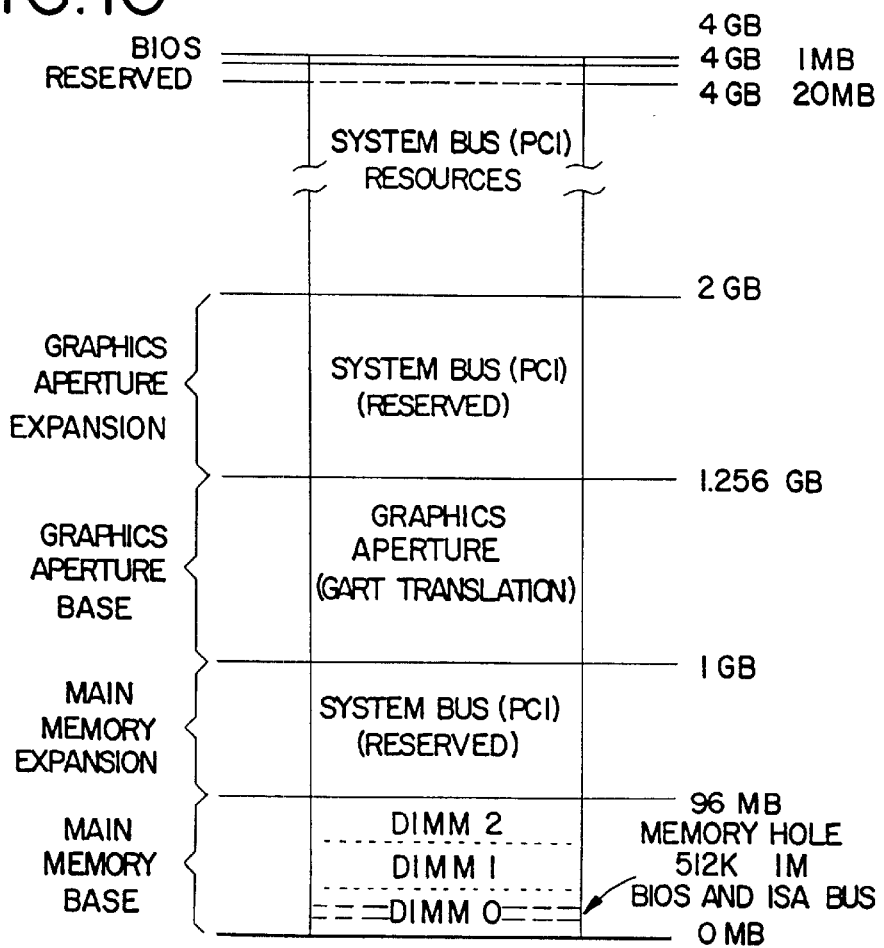

ULTRASONIC SYSTEM AND METHOD FOR STORING DATA

This application is a division of application number 09/001,489, filed Dec. 31, 1997, U.S. Pat. No. 6,171,244.

BACKGROUND

This invention relates to an ultrasound system and method for processing data. In particular, the method and system provide for processing, transferring, and storing ultrasound data, control data, and other information.

Ultrasound systems acquire, process, and store acoustic information. The acoustic information is used to generate various types of images and other data. Typically, ultrasound imaging systems include several dedicated data processing structures, including one or more digital signal processors (DSP) for processing the acoustic data and one or more microprocessors for system control. The control microprocessors provide control instructions to the data processing structures. The control instructions are generated in response to operating system software, user interface input, and other communication and control software. One or more separate memory blocks provide bulk storage for CINE operations, storing acoustic data generated by the various data processing structures. The memory blocks are designed to support the specific volume and bandwidth of the real time data stored in and retrieved from them. A separate memory is used for storing the microprocessor software. As a result, the microprocessors do not have direct and efficient access to acoustic data during real time operation of the ultrasound system, and many different memories are required.

Another example of the separation of memories is the use of various display refresh memory planes for generating an image. Ultrasound systems typically employ separate display refresh memory planes for each of combination control information, text and graphics information, waveform information, and image information. The stored information is output from each of these memories at a constant rate to update and refresh the display. Due to different reconstruction and display requirements for the different types of data, the refresh memory planes are separated. Text and graphics information is generally constructed by a microprocessor and written into the text and graphics refresh memory plane. Image and waveform data are generally constructed by some combination of dedicated hardware and DSP processing. The image and waveform data are then stored in their respective memory planes. The output from the refresh memory planes is combined and displayed.

One example of an ultrasound system is disclosed in U.S. Pat. No. 4,662,222 (the '222 patent). The '222 patent describes various models for reconstructing an acoustic image using inverse scattering techniques. Beginning at column 19, line 14, the system for generating the acoustic image is described. The system includes a CPU and an array processor to control the electronic system in accordance with the flowcharts shown in FIGS. 6A–6F. At lines 25–28, the disclosure notes that "special purpose computational hardware should be constructed to incorporate the flow diagrams of FIGS. 6A–6F." The appendix of the '222 patent discloses a program to solve the inverse scattering models by the array processor. The CPU's control of the system to solve the inverse scattering models is then described with reference to FIGS. 6A–6F.

Some ultrasound systems combine various memory structures and processing structures. For example, U.S. Pat. No. 5,492,125 discloses two multi-processors for processing acoustic data. The multi-processors share a memory. The memory is accessed through a cross-bar. One multi-processor receives acoustic data and partially processes the data. The partially processed data is stored in the shared memory. The other multi-processor obtains the partially processed data and completes the processing.

Multi-processors are used in systems other than ultrasound systems. For example, multi-processors are used in personal computing. Various multi-processors are known, such as Pentium Pro®, Pentium II®, and other 686 class microprocessors that support multi-processing, and that use single instruction multiple data processing. For use with graphics intensive computers, interface devices such as the Intel® Accelerated Graphics Port chip set are used to provide high speed interactions between graphic accelerators, multi-processors and memories.

SUMMARY

The present invention is defined by the following claims, and nothing in this section should be taken as a limitation on those claims. By way of introduction, the preferred embodiment described below includes an apparatus and method for processing ultrasound data. The apparatus includes an interface operatively connected to a memory, a processor, a source of acoustic data (such as a data bus) and a system bus. The memory stores data from the processor, ultrasound data from the source, and data from the system bus. The processor has direct access to the memory. In another embodiment, the system bus has direct access to the memory.

In other embodiments, a memory stores both ultrasound data and various of: beamformer control data, instruction data for the processor, display text plane information, control plane data, and a table of memory addresses.

Other embodiments are possible. Further aspects and advantages of the invention are discussed below in conjunction with the preferred embodiments.

BRIEF DESCRIPTION OF THE DRAWINGS

FIG. 5 is a block diagram of one embodiment of a portion of the data processing system of FIG. 2, including a video reconstruction data path.

FIG. 6 is a block diagram of a multi-processor system for use in the data processing system of FIG. 1.

FIG. 9 is a flow chart representation of a processor functions.

FIG. 10 is a representation of a memory map of one embodiment.

DETAILED DESCRIPTION OF PREFERRED EMBODIMENTS

Figure 1:
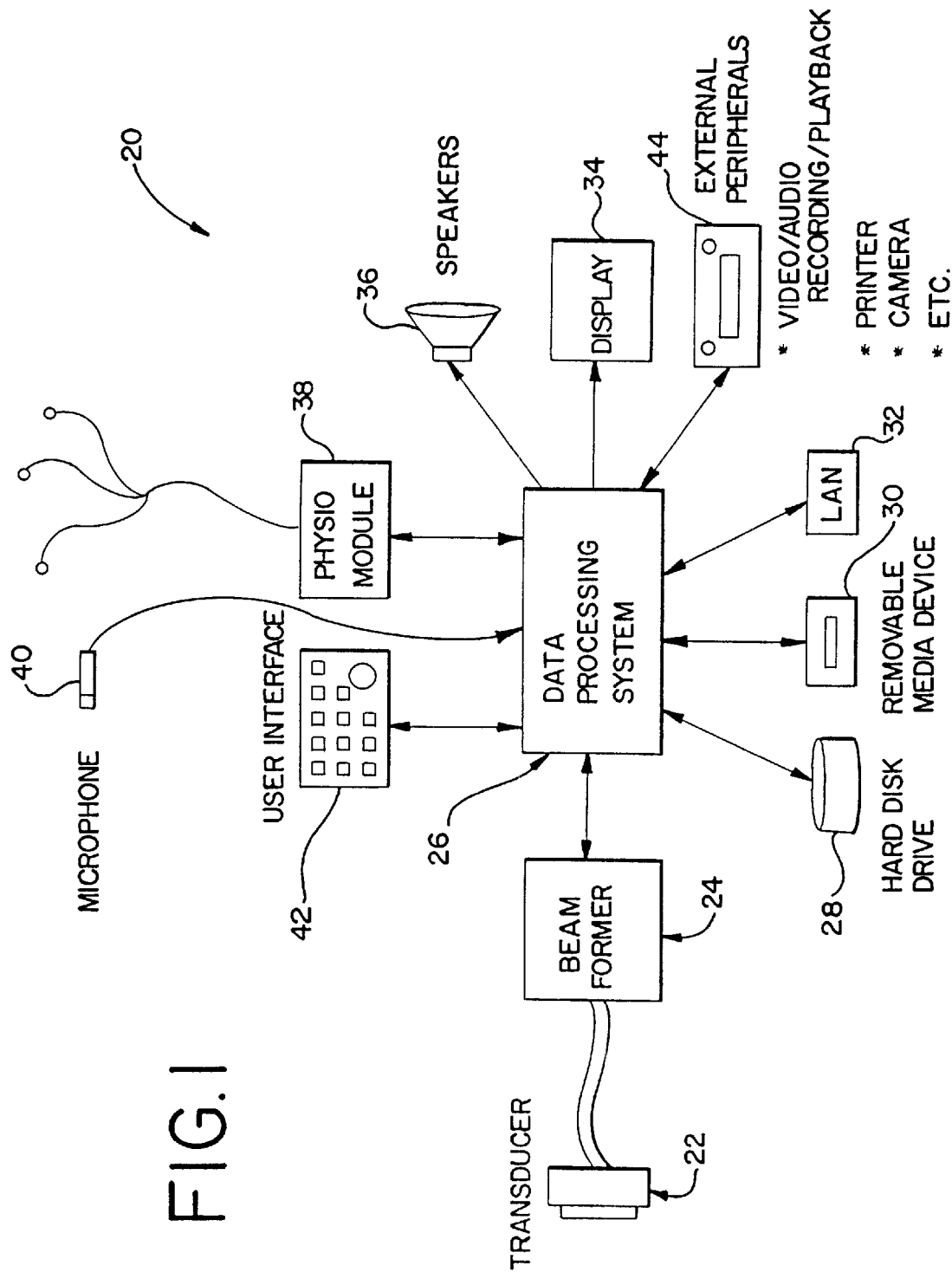
FIG. 1 is a block diagram of an ultrasound imaging system, including various peripheral components.

Referring to FIG. 1, a preferred embodiment of an ultrasound system according to the present invention is generally shown at 20. The flexible system 20 is described below, first with reference to the structure of the system 20, and then with a reference to several examples of the operation of the system 20. Other structures and uses of the system 20 are intended to be covered by the claims, which define the invention.

I. Structure

A. General

The system 20 includes a transducer 22, a beamformer 24 and a data processing system 26. The system 20 also includes various peripherals, such as a hard disk drive 28, a removable media device 30 (e.g. a magneto optical disk drive), a local area network 32, a display 34, a speaker 36, a physio module 38, a microphone 40, a user interface 42 and other external peripherals 44. The other external peripherals include video or audio recording and playback devices, printers, cameras, and other devices. The peripherals may include analog or digital video or audio inputs and outputs. The physio module 38 preferably includes an EGG, phono, pulse, respiration and one or more auxiliary DC-coupled input channels (e.g. DC-A, DC-B, DC-C and DC-D). Preferably, the data processing system 26 controls operation of the peripherals. The system 20 may include no peripherals or any subset of these peripherals.

The data processing system 26 includes a centralized memory for storing microprocessor code and data (software or algorithms) and concurrently storing various subsystem data. The subsystem data includes acoustic image data, video data, audio data, physio data, waveform data, text and graphics data, and other subsystem data.

As used herein, the term ultrasound or acoustic image data encompasses data derived from the transmission of acoustic energy and used to generate an image or audio output in one or more of various modes, such as B-mode, M-mode, color Doppler mode (velocity, variance or energy), spectral Doppler mode (spectrum, derived waveform or audio) and other modes. Ultrasound image data includes acoustic data from the beamformer 24 (e.g. in phase and quadrature data or real value data), fundamental or harmonic frequency based data, or acoustic data at various stages of processing (e.g. detected data, filtered data, weighted data, thresholded data, video data (compressed or uncompressed), combined data, and other processed data derived from acoustic data from the beamformer). The type of ultrasound image data (the stage of processing of the data) is referred to herein by the type of processing, the source or the component used to process the data. For example, harmonic data is ultrasound image data associated with harmonic frequencies of transmitted fundamental frequencies. As another example, beamformer data is ultrasound image data provided by a beamformer. Ultrasound data includes ultrasound image data, audio data (e.g. physio audio, microphone audio and VCR audio), waveform, physio, video (compressed or uncompressed), text and graphics, patient and control data used or generated in an ultrasound system.

The data processing system 26 also includes a microprocessor or parallel microprocessors in a symmetric multiprocessing structure for controlling the system and processing ultrasound image data stored in the centralized memory. The microprocessor operates in response to or executes instruction code and data also stored in the memory.

Based on control instructions from the data processing system 26, the beamformer 24 generates electrical signals. The electrical signals are applied to the transducer 22. The transducer 22 transmits acoustic energy and receives echo signals. Electrical signals corresponding to the echo signals are provided to the beamformer 24 from the transducer 22. The beamformer outputs ultrasound image data, such as in phase and quadrature (I and Q) data associated with a plurality of ranges along one or more scan lines.

The data processing system 26 processes and stores the ultrasound image data from the beamformer 24. Processing includes altering the data before, after or as part of a reconstruction or scan conversion and output to the display 34. For example, color Doppler information is detected from the I and Q ultrasound image data, and the detected ultrasound image data is stored. The stored ultrasound image data is then temporally or spatially filtered or otherwise processed. The processed ultrasound image data is also stored and output for reconstruction.

Other than the beamformer 24, one or more peripherals may provide ultrasound data to the data processing system 26. The external peripherals may also receive ultrasound data from the data processing system 26, such as audio data or video ultrasound image data. The hard disk drive 28 and the removable media device 30 provide and store software, ultrasound data and other information for the data processing system 26. A local area network (LAN) also supports the transfer of software or ultrasound data to or from the data processing system 26. For example, operating system code, patient data, parameter data, control data or image data is transferred. The user interface 42 provides or receives information about the status of the various user controls or displays (lights or other secondary displays on the user interface 42). The physio module 38 provides patient physiological data and event (trigger) information to the data processing system 26, as well as the state of any user controls located on the physio module 38. Various physio modules 38 may be used, such as an ECG or respiration device. Data for operation of the physio module 38 is communicated from the data processing system 26 or another source. The microphone 40 allows for voice activated control of one or more user selectable functions as well as the input of patient data, such as verbal annotations. Information, such as ultrasound data, control and parameter information, or patient information may be provided from any of these or other peripherals.

B. Data Processing System

Figure 2:
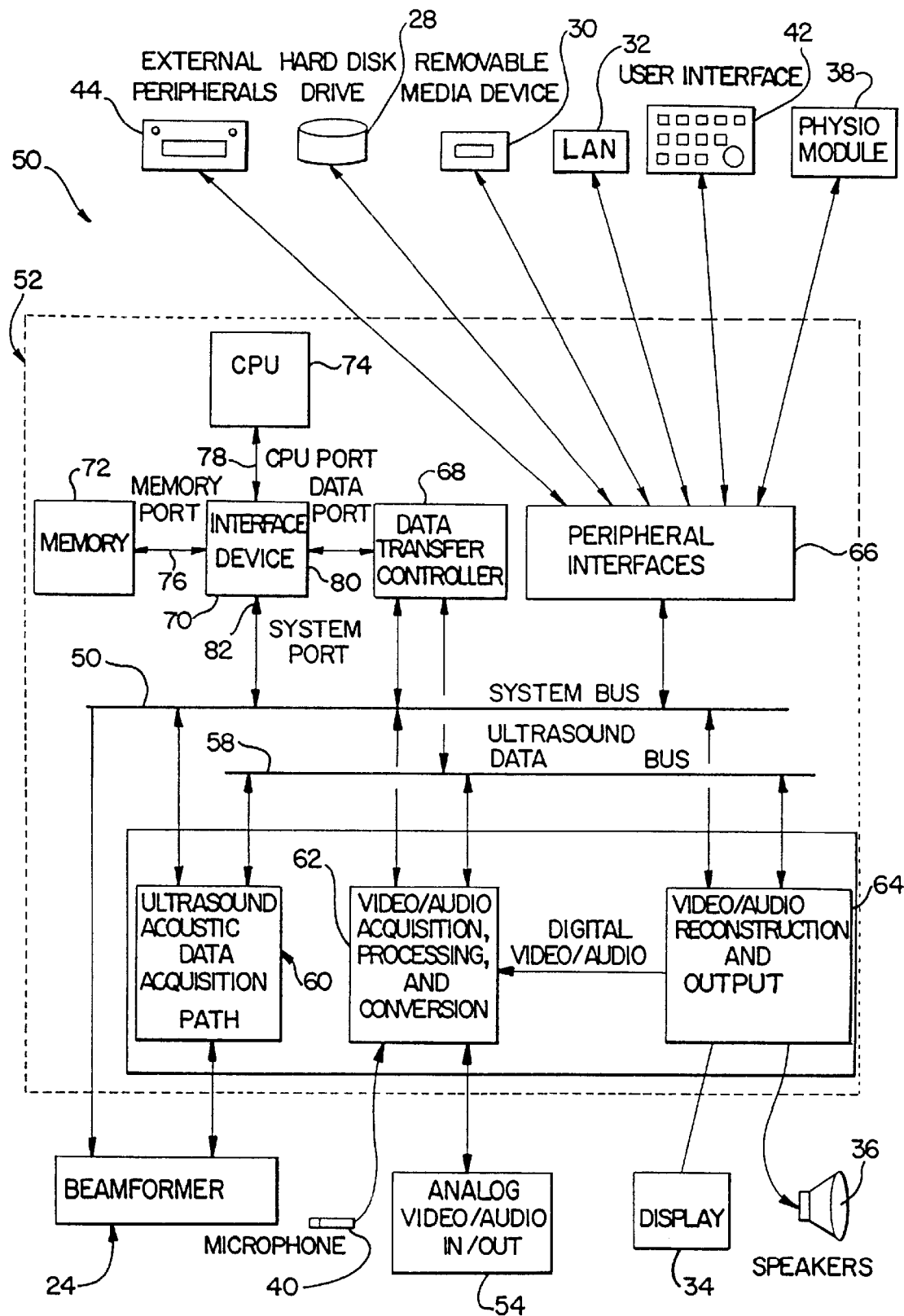
FIG. 2 is a block diagram of a data processing system of FIG. 1, including various peripheral components.

Referring to FIG. 2, a preferred embodiment of an ultrasound system according to the present invention is shown generally at 50. As used herein, an ultrasound system or apparatus 50 includes no, one or more peripherals. Likewise, the ultrasound apparatus or system 50 may include or exclude the beamformer 24. The system 50 preferably includes a data processing system 52, the beamformer 24, and various peripherals. The various peripherals include one or more of the hard disk drive 28, the removable media device 30, the LAN 32, the display 34, the speakers 36, the physio module 38, the microphone 40, the user interface 42, the external peripherals 44, an analog video or audio peripheral 54 and any other peripherals. Preferably, the beamformer 24 includes a multiplexer for switching between receive and transmit processing. The beamformer 24 comprises transmit and receive beamformers. In this embodiment, the receive beamformer is operatively connected to provide acoustic data, and both transmit and receive beamformers receive and are responsive to control and parameter information from the data processing system 52.

The data processing system 52 includes various ultrasound data paths and system data paths. As used herein, a data path is one or more components for receiving, processing or transferring data. Any of these various data paths may be responsive to information from other data paths.

As used herein, the term "responsive to" is intended to broadly cover any situation where a first component alters its operation in response to a signal generated by a second component whether directly or indirectly. Thus, the first component is said to be responsive to the second when the first component responds directly to an output signal of the second component. Similarly, the first component is responsive to the second if intermediate components or processors alter or modify a signal of the second component before it is applied as an input to the first component.

The data processing system 52 includes a system bus 56 and an ultrasound data bus 58. An ultrasound acoustic data acquisition path 60, a video/audio acquisition, processing and conversion path 62 (video/audio acquisition data path 62), and a video/audio reconstruction and output path 64 are connected to both the system data bus 56 and the ultrasound data bus 58. These connections allow the transfer of ultrasound data or system communication, control and parameter data between various components of the system 50. The ultrasound data acquisition path 60 also connects with the beamformer 24. The video/audio acquisition path 62 preferably also connects with the analog video/audio peripheral 54, the microphone 40 and the video/audio reconstruction path 64. The video/audio reconstruction path 64 also connects with the display 34 and the speakers 36. The system bus 56 also connects with the beamformer 24 and one or more peripheral interfaces 66.

A data transfer control device 68 also connects to both the system bus 56 and the ultrasound data bus 58. An interface device 70 connects to the data transfer controller 68, the system bus 56, a memory 72, and a CPU 74.

Figure 13:
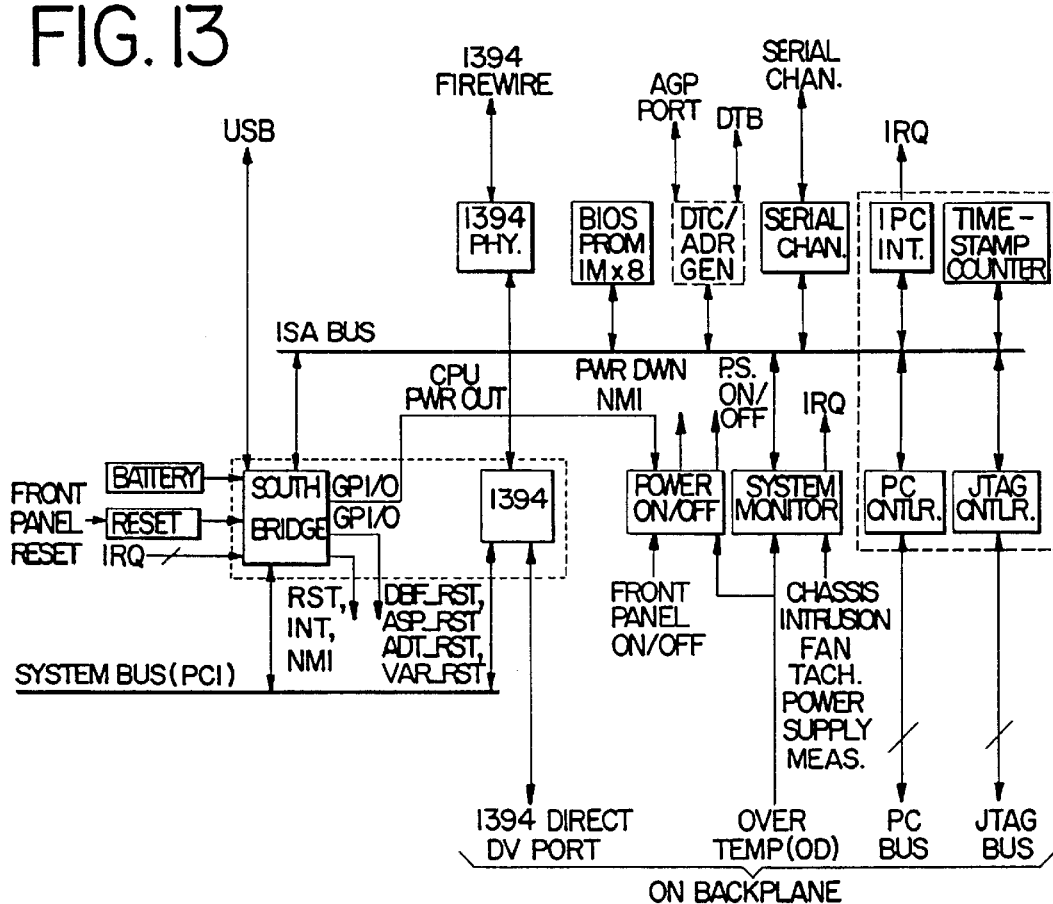
FIG. 13 is a block diagram of one preferred embodiment of a south bridge configuration.
Figure 14:
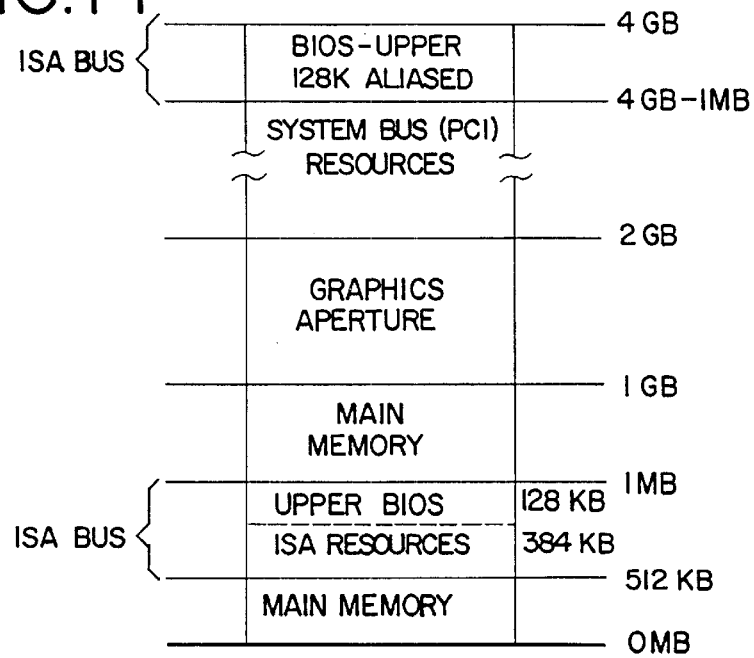
FIG. 14 is a representation of a memory map of one embodiment.

In one preferred embodiment, the various components of the data processing system 52 are on three boards (a mother board and two daughter boards). For example, the data transfer control device 68, the interface device 70, the memory 72, the CPU 74 and the peripheral interfaces 66 are located on the mother board, so that these components (e.g. the interface device 70 and the south bridge (see Section C and FIG. 13) of the peripheral interfaces 66) are grouped together. In this example, the ultrasound acoustic data acquisition path 60 and the video/audio acquisition data path 62 are on one daughter board, and the video/audio reconstruction path 64 is on the other daughter board. Other component partitioning may be used.

The interface device 70 controls access to the memory 72. Preferably, the interface device 70 is a quad port or other bridge device, such as the Intel® 82443LX, Intel® 440BX, or a Via Technologies Inc. VT82C597 PCI Accelerated Graphics Port (AGP) controllers. AGP is a specification or protocol prepared by Intel®. The interface device 70 preferably includes a physical address generator for controlling the memory 72. Other devices with more or fewer ports operating pursuant to the AGP or other specifications may be used (e.g. three ports or a PCI local bus protocol).

The interface device 70 interfaces between the memory 72, the CPU 74, the data transfer controller 68 and the system bus 56 through a memory port 76, a CPU port 78, a data port 80 and a system port 82, respectively. As used herein, a port is a connection or other interface for the transfer of data to or from a component. Preferably, the CPU port 78 comprises a microprocessor host interface with at least a 60 Mbytes/sec connection (e.g. 64 bit data path at 96 MHz). Preferably, the memory port 76 comprises a 64 bit wide data path with a 64 or 96 MHz clock with at least a 190 Mbytes/sec connection. The system port 82 comprises a PCI bus interface with at least a 30 Mbytes/sec connection (e.g. 32 bit data path at 32 MHz). The data port 80 comprises an AGP interface with at least a 100 Mbytes/sec connection (e.g. 32 bit data path at 64 MHz). The data port complies with Intel's Accelerated Graphics Port Interface Specification (revision 1.0 or later), but in alternative embodiments may employ any data transfer mechanism meeting the bandwidth and requirements discussed above or other appropriate requirements. Preferably, the data port 80 supports burst transfers of packets of ultrasound data with logical and implicit sequential addressing of successive data values to facilitate high through put and transfer efficiency.

The bandwidths discussed above are approximations and may vary as a function of various factors, including programming and system capabilities. Other effective bandwidths, bus widths, and clock rates may be used. Preferably, synchronization signals are used for transferring data between two different clock domains (e.g. 64 MHz to or from 48 MHz).

Alternatively, the interface 70 comprises other port designs, such as supporting different protocols, different connection speeds or different data widths. For example, a three port device without a data port 80 is used. In this example, the ultrasound data bus is eliminated and ultrasound data transfers are performed over the system bus 56.

The interface device 70 arbitrates between ports, translates interface signals, buffers data, controls the memory 72, routes data between the various ports and any sub-set of these functions. Preferably, the interface device 70 is operable to transfer data between the CPU port 78 and the memory or system ports 76 and 82, and to transfer data between the system or data ports 82 and 80 and the memory port 76. In alternative embodiments, the interface device 70 transfers between the CPU and data ports 78 and 80 or between the data and system ports 80 and 82.

The interface device 70 provides direct access to the memory 72 from the CPU port 78, the data port 80, and the system port 82. The CPU 74 can directly fetch instructions from memory 12 for execution, and data for processing. The memory 72 is accessed by the CPU 74 as standard random access memory in the CPU's 74 memory address space. Preferably, the access is formatted for pipelined addressing of four or more quad words or other sequences of data for improved throughput.

Accesses to the memory 72 from the system port 82 also support direct memory read and write access through single read or write transactions on the system bus 56 in the memory's 72 address space. Preferably, the system port 82 of the interface device 70 supports and controls (e.g. arbitration time out, parking and configuration cycle generation) burst transfers on the system bus 56 according to the PCI local bus specification, where a burst is comprised of multiple single transactions with implicit sequential addressing after the first transaction.

Accesses to the memory from the data port 80 also support direct memory access. Preferably, transfers on the data port 80 to or from the memory 72 employ pipelined transactions according to the AGP specification, where the transaction request, size, and address are supplied to the interface device 70 by the data transfer controller 68 over a set of sideband signals. Preferably, the graphic aperture (memory window) is at least 256 Mbytes. The data transfer is subsequently performed by the interface device 70 over the data port data bus in response to the request. Transaction requests can be made concurrently with data transfers using separate sideband data signals.

The memory 72 accepts data from or provides data to the CPU 74, the data transfer controller 68 and the system bus 82. The memory 72 comprises a synchronous DRAM (SDRAM) memory, such as a Texas Instruments'TMS 626162. Alternatively, a SDRAM-II, Double Data Rate SDRAM (DDR SDRAM), a sync-link DRAM (SL-DRAM), a RAMBUS DRAM (RDRAM), Direct RDRAM, Multi-Bank DRAM (MDRAM), Cache Enhanced SDRAM (ES-DRAM), or a non-synchronous memory is used. The memory 72 may comprise one or more memory components and one or more modules, such as three 32 Mbytes DIMM modules. Each memory component is associated with physical locations in the memory 72. Preferably, all of the memory components operatively connect to and are controlled by the interface device 70 (one memory). Less than all or other sources of control may be used. The memory port 76 of the interface device 70 comprises a memory port 96 of the memory. More than one memory port 96 may be used.

Figure 3:
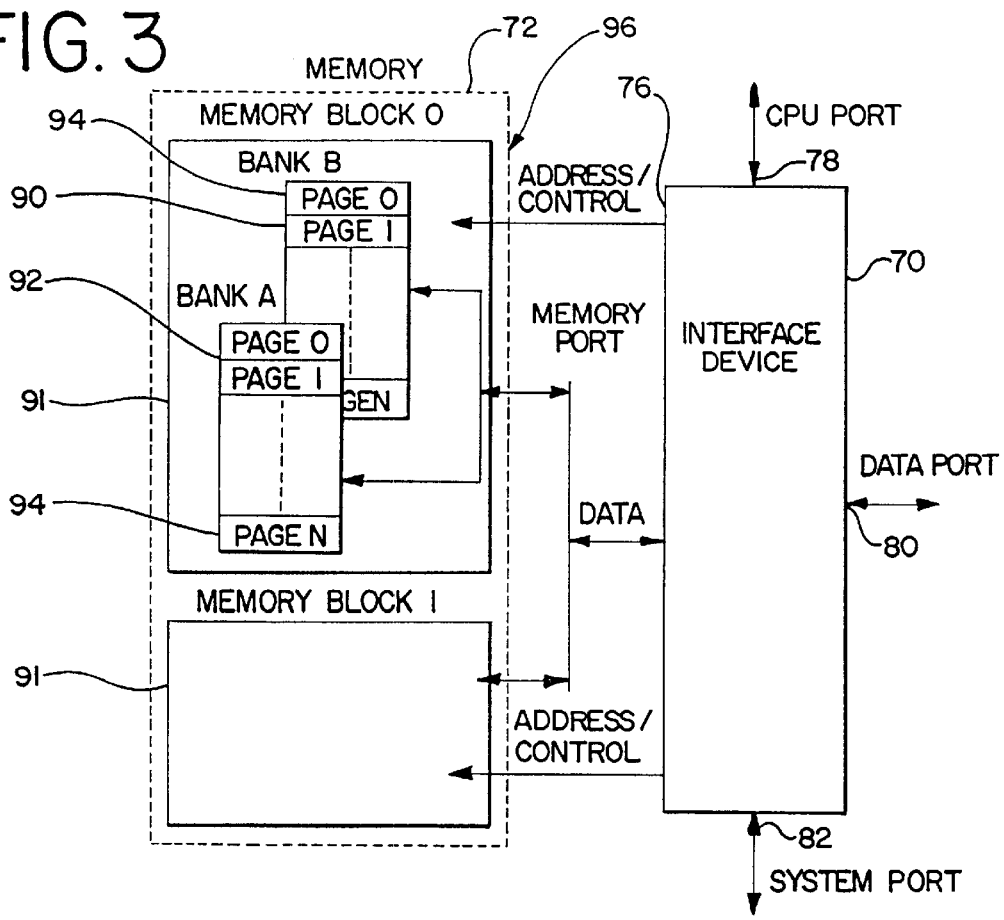
FIG. 3 is a block diagram of one embodiment of a memory and an interface device of FIG. 2.

Referring to FIG. 3, the memory preferably comprises two memory banks 90 and 92 in one or more blocks 91. More or fewer banks 90, 92 or blocks 91 may be used. Preferably, each bank 90, 92 comprises one or more pages 94.

Referring to FIG. 2, the memory 72 provides storage for CPU code and data, ultrasound image data from the data transfer controller 68, the CPU 74, or the system bus 56, and other data provided from the CPU 74, the data transfer controller 68, or the system bus 56. Other data may include text, graphics or control plane data for display, audio data, control and parameter data, messaging data, and patient information. Preferably, one area or section of the memory 72 is dedicated to CPU code and data and interprocessor communication and control data. As shown in FIG. 10, a 4 GB address range is used, but other ranges may be used. From 512 Kbytes to 1 Mbyte, legacy components (DOS compatibility) are located in the system addresses space. In FIG. 10, BIOS represents the system boot and configuration ROM occupying 128 kB within the 512 kB to 1 MB range and 1 MB at the top of the 4 GB address range. Resources connected to the system bus 56 are accessed in the 2 GB to 40 GB-20 MB range. Preferably, at least 64 Mbytes of memory is dedicated to acoustic, waveform, text and graphics, and video storage. Other memory allocations and maps may be used.

The CPU 74 is a programmable processor operable to run operating system, user interface, communication, control, applications and ultrasound data processing software or any sub-set of this software. Preferably, the CPU 74 is a 32 or 64 bit single instruction multiple data processor (SIMD), such as Intel's Pentium II® processor (e.g. 350 MHz with a 100 MHz frontside bus and 512 Kbytes of L2 cache integrated in a slot 1 single edge contact cartridge). As used herein, single instruction multiple data processors are processors capable of applying a single instruction on multiple data, such as in parallel processing paths. Furthermore, a multi-media extension (MMX) SIMD processor may be used. Other processors may be used, such as by other manufacturers, with 32 bits, or without SIMD capability.

Preferably, a cache memory is internal to and managed by the CPU 74, but in alternative embodiments the cache memory may reside on a host-bus and be managed by the interface device 70. Other embodiments may contain both CPU internal cache and host bus cache which are managed by either the CPU 74, interface device 70, or both. The cache memory reduces transfers to memory 72 on the CPU port 78 and improves performance for instructions and data that are repeatedly used. The cache memory of the CPU 74 temporarily stores ultrasound data, such as image data, for processing by the CPU 74. Upon completion of the processing, the ultrasound data is stored in the memory 72. Additional ultrasound data is then stored in the cache of the CPU 74 for undergoing the same processing. Furthermore, the cache memory may contain both instructions for execution by the CPU 74 as well as ultrasound data, such as image data.

The host bus connects to the CPU port 78 of the interface device 70. The CPU 74, using the host bus, obtains software data (instruction code) from the memory 72 for execution. The CPU 74 operates or executes pursuant to the software data.

In an alternative embodiment, the CPU 74 comprises two or more microprocessors. Referring to FIG. 6, two symmetric processors 100 and 102 are shown. Preferably, the processors 100 and 102, such as Intel's Pentium® processors, operate pursuant to a symmetric multiprocessing protocol. For example, Intel's multi-processor specification (version 1.4 May 1997) defines the use. Preferably, a master slave relationship or any other hierarchy or geometry limitations on processing and communications is not created between the processors 100 and 102. The processors 100 and 102 share the same memory space and access the memory 72 with the same addresses. This memory symmetry allows both processors 100, 102 to execute a single copy of the operating system (instruction code and data) stored in the memory 72. The processors 100 and 102 also share access to the same input and output subsystem, such as a CPU or host bus 104 and the associated input and output ports and interrupt controllers. This input/output symmetry allows either processor 100 and 102 to receive interrupts from any other component of the system 52. Other types of symmetry pursuant to the same or different multi processing protocols may be used. For example, memory symmetry, but not I/O symmetry may be employed.

Referring to FIG. 2, the CPU 74 initiates transfers on the system bus 56 through the interface device 70. Preferably, the system bus 56 is a high performance multi-master bus, such as a PCI local bus (revision 2.1 or later) with Industrial Computer Mfg. Group Compact PCI (revision 2.0) mechanical components and connector technologies. The system bus 56 may comprise other multi-master or non-multi-master buses. The system bus 56 provides a data path for the transfer of communication, control, parameter and other information between any master or initiator and any slave or target resource connected to the system bus 56. The system bus 56 also transfers other data, such as patient, ultrasound data and instruction code data, to the memory 72. Preferably, any transfer of data on the system bus 56 targeted for storage in the memory 72 passes through the system port 70. Alternatively, the data passes through the data port 80.

The system port 82 of the interface device 70 preferably includes system bus arbitration and control logic. Preferably, the system port 82, the peripheral interfaces 66, ultrasound acoustic acquisition path 60, the video/audio acquisition path 62, video/audio reconstruction path 64 and the beamformer 24 are operable to act as the master/slave or both master and slave resources on the system bus 56. Preferably, the CPU 74 is capable of locking (uninterrupted multi-transfers) the memory 72 pursuant to the PCI specification, but other resources may use other means for assuring proper operation when accessed by multiple bus masters. Other connections between the system bus 56 and other resources of the data processing system 26 or peripherals may be provided.

Control, communication and parameter data is formatted as appropriate for its purpose. Other control data includes reset signals for processors, boards and the system 50 distributed under the control of the CPU 74. Furthermore, timing information (e.g. VCR annotation (counter) update data), and interrupt data (e.g. to identify frames of display data, physio triggers, vertical blanks, and power failure) is managed by the CPU 74.

Local mailbox memories, such as 64K×32 memories, may be provided as local resources in the paths connected to the system bus 56 for temporarily storing communication, control and parameter data. Preferably, interprocessor communications are buffered in the memory 72 and employ either point-to-point dedicated communications or common resources with software arbitration, but alternatively may employ only the mailbox memory or a combination of the memory 72 and the local mailbox memory for interprocessor communication.

The peripheral interfaces 66 allow communication and transfer of data from any of the various peripherals to the system bus 56. For a block diagram of the peripheral interfaces 66, see the attached Section C. The south bridge of Section C and FIG. 13 preferably comprises an Intel 82371 AB (PIIX4 or X6). The peripheral interfaces 66, such as the south bridge, may perform subtractive decode for any transactions below 16 Mbytes on the system bus 56 pursuant to the PCI bus specification.

Preferably, the peripheral interfaces 66 comprise one or more industry standard interfaces, such as an RS-232 serial interface, an IEEE Std. 1394-1995 (Firewire) interface, a Universal Serial Bus (USB) interface or an Ethernet 10/100 base T interface. Preferably, one or more high bandwidth Firewire interfaces connect to any hard disk drives 28, removable media devices 30 or other peripherals supporting the Firewire standard, such as a digital VCR. Furthermore, the Firewire interface may connect to the video/audio acquisition data path 62 for direct transfers of digital video data. Preferably, the Firewire interface includes an Open Host Controller Interface Specification compatible device.

One or more lower bandwidth USB interfaces connect to any physio modules 38, user interfaces 42, and other peripherals supporting the USB standard, such as printers and cameras. Preferably, the USB interfaces include a controller compatible with the Universal Host Controller Interface guidelines. Using a USB interface, the physiological or patient data acquired in real time from the physio module peripheral 38 is transferred over the system bus 56 for storage in the memory 72.

One or more 10/100 Base-T Ethernet interfaces, such as AMD's AM 79C973 10/100 Mb PCI interface Ethernet controller with integrated physical layer interfaces, connect to one or more computers or networks, such as the LAN 32. Preferably, the Ethernet interface directly connects to the system bus 56 for direct memory access burst transfers to or from the memory 72. LED's are preferably provided to indicate the Ethernet interface status. A standard RJ45 connector is provided for the LAN 32 connection, but other LAN 32 connections may be used.

Information from any of the various other peripherals is transferred through the peripheral interfaces 66 to the system bus 56. By using standardized interfaces, the number of distinct interfaces required in the system is reduced and may facilitate testing of the data processing system 52 through the peripheral interfaces 66. Furthermore, JTAG, and I²C serial busses or other busses are connected to various resources or boards to facilitate testing, system monitoring (temperature), and board level identification and control.

Figure 7:
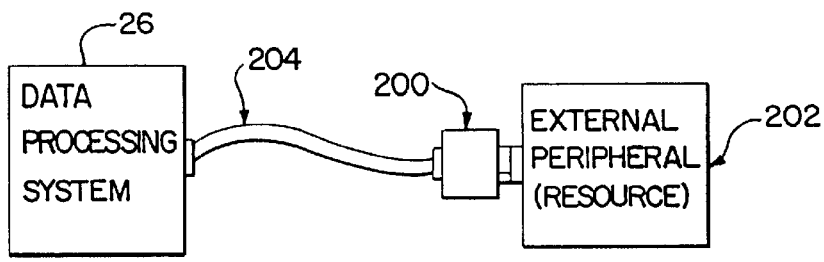
FIG. 7 is a block diagram of a peripheral connection.

As an alternative, the peripheral interfaces 66 include one or more non-standard interfaces. As an alternative to non-standard interfaces, adapter modules as shown in FIG. 7 at 200 are used. Depending on the non-standard data and physical interface of any external peripheral 202, the physical plugs and circuitry of the adaptor module are configured to allow connectivity and the transfer of data.

The adaptor module 200 is shown connected between an external peripheral 202 and the data processing system 26. Preferably, the adaptor module 200 connects directly to the external peripheral 202 and connects to the data processing system 26 through a standard communication interface cable 204. In alternative embodiments, a cable is provided between the adaptor module 200 and the external peripheral 202, and the adaptor module 200 connects directly or through another cable to the data processing system 26. The external peripheral 202 includes one or more peripheral devices, including any of the peripherals discussed above.

The adaptor module 200 is preferably powered by the peripheral interface 66 (see FIG. 2) of the data processing system 26, such as a Firewire or USB interface. The IEEE Std. 1394-1995 (Firewire) (e.g. 8–40 volts at 1.5 amps per port) and USB (e.g. 5 volts ±5% at 500 mAmps per port) serial buses and associated interfaces include provisions for powering external devices. Preferably, three Firewire and two USB ports are used, and current limited, such as with resetable overcurrent protection.

The adaptor module 20 preferably connects to non-standard physical plugs associated with the external peripheral 202 and performs communication, control, data, and interface signal translation to or from the external peripheral 202. For example, data from a non-standard video page printer is translated to conform with the standard Firewire or USB interface. Likewise information provided from the data processing system 26 to the external peripheral 202 is translated for use by the external peripheral 202.

Other than the system bus 56 and peripheral interfaces 66, the ultrasound data bus 58 comprises a data path for transferring ultrasound data between any of various paths and the memory 72. Preferably, the ultrasound data bus 58 is a 32 bit synchronous bus operating at 48 MHz and allowing 48 requesters. In one embodiment, the maximum, minimum and granularity of data packets on the data bus 58 is 1024, 256 and 16 bytes, respectively, but other values may be used. The ultrasound data bus 58 preferably comprises separate transfer request and data transfer signal lines and any request has a maximum latency of 100 μsec. This separation permits requests for transfer to be performed independently from and overlapped with actual transfers of ultrasound data. Preferably, the bandwidth of the bus is approximately 160 Mbytes (192 Mbytes/sec with 85% efficiency) and is distributed for various data (e.g. in Mbytes/sec: B/M-mode - 12, F-mode-6.67, D-mode-.28, full video image capture-8, full video review-32, 3 size review-8, VCR playback-24, Image reconstruction-24 to 32, Text, graphics and display field control reconstruction-36 and physio/derived waveform/audio reconstruction-.25). Distribution is preferably maintained through uniformly distributed requests. Other data buses may be used, including buses configured for different numbers of requesters, clocks, bit widths, and request latencies.

Figure 8:
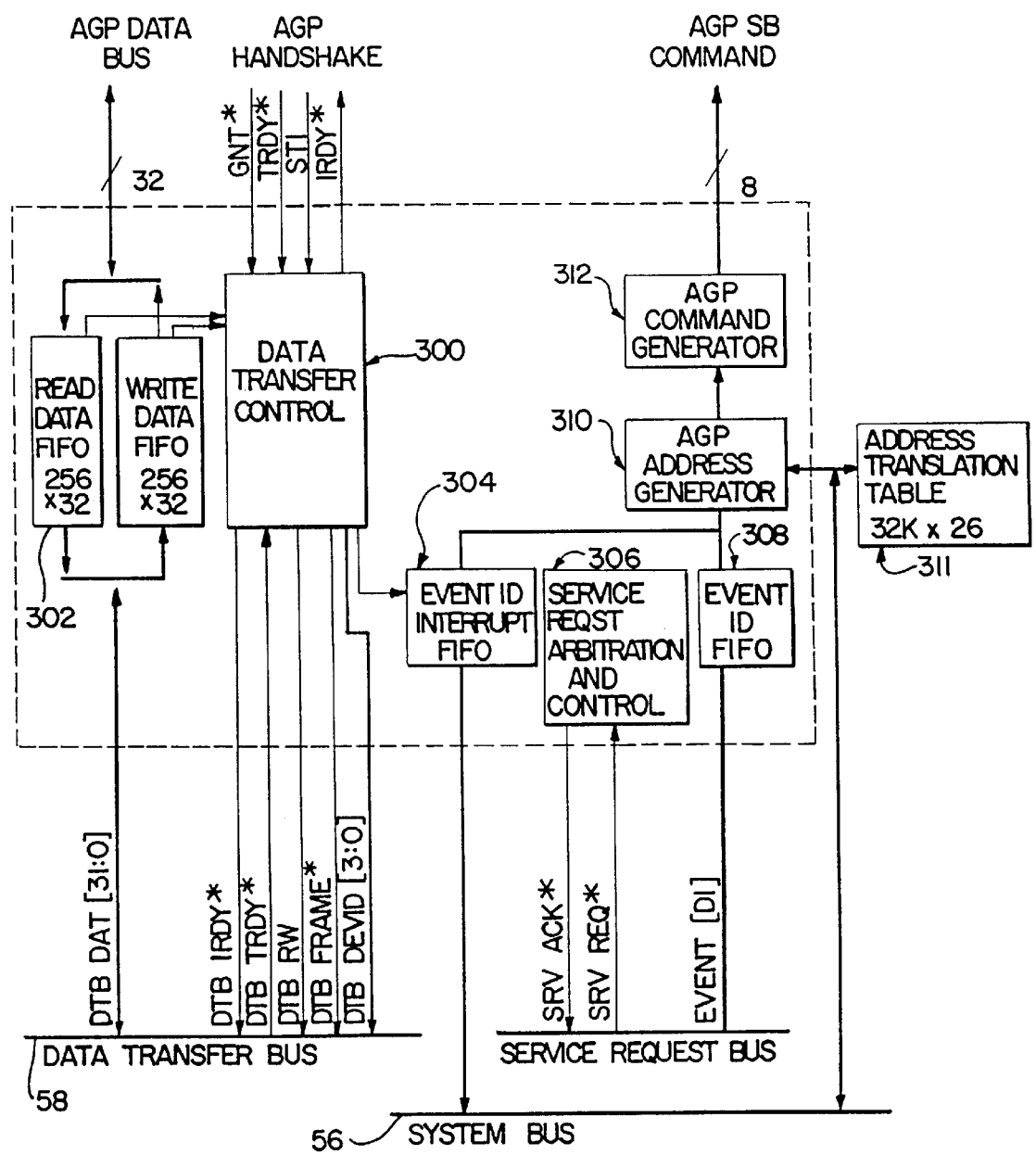
FIG. 8 is a block diagram of one embodiment of a data transfer controller of FIG. 2.
Figure 11:
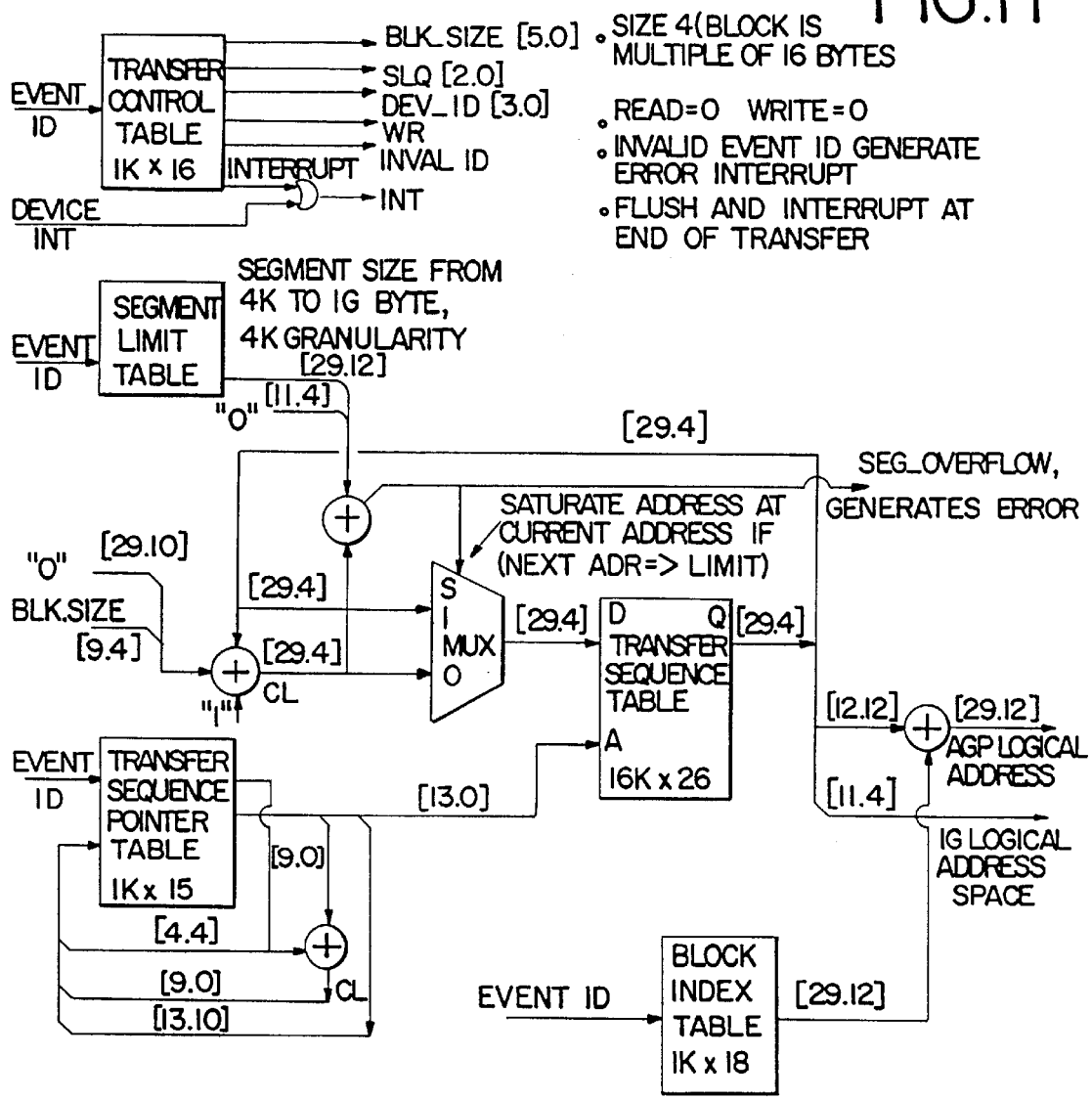
FIG. 11 is a block logic diagram of one preferred embodiment for address generation.
Figure 12:
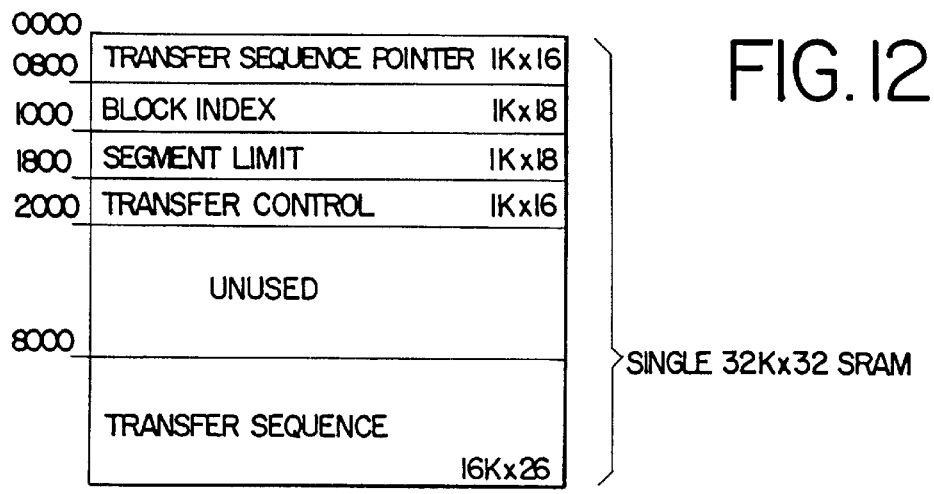
FIG. 12 is a representative memory map for an address generator table of one preferred embodiment.

An ultrasound data path may include the data transfer controller 68. Referring to FIG. 8, the data transfer controller 68 preferably includes a controller 300, read and write buffers 302, an interrupt buffer 304, a service controller 306, an Event ID buffer 308, an address generator 310, and a AGP command generator 312. To transfer data, an event ID is stored in the event ID buffer 308 (FIFO) when a request for transfer is made. The control 300 uses the event ID to access transfer control parameters, including generation of logical addresses. FIG. 11 shows a logical diagram for address generation as discussed above and FIG. 12 and Section B show an associated memory map for an address generator table 311. Preferably, address generation is done in parallel (address generation for the next event is done during data transfer for the current event).

The address generator 310 generates the logical addresses based on the control parameters. The results are provided to the AGP command generator 312. The AGP logical address is generated by a sequential process of table reads and computations. The 30-bit AGP logical address (1 Gbyte) consists of an 18-bit segment address and the remaining 12 bits point to a location within a 4 Kbyte segment. The 18-bit logical segment address is computed by adding a memory Block Index pointer for the event ID to the output of the address table. Additionally, the address table output is added to the block size to compute the base address for the next transfer for the event ID. This allows successive block sequential transfers to access main memory 72 in a logically contiguous address space while using the same event ID.

For block non-sequential transfers, the address table is not rewritten. The amount of data is determined for generating the next sequential address. After each block non-sequential transfer, the 10 least significant bits are incremented to generate a new address table address, allowing subsequent transfers with the same event ID to access main memory 72 in a non-contiguous manner within the selected segment.

The AGP command generator 312 requests transfer to or from the main memory 72 over an AGP sideband command bus and tracks the interface device 70 to prevent overflow. The sideband command bus, as specified in Intel's AGP specification, demultiplexes the address and data busses. Preferably, the command requests correspond to 16 byte transfers, but other sizes may be used.

The read or write buffer 302, such as 256X32 FIFOs, transfer the data under control of the controller 300 and convert data rates (e.g. from the 64 MHz data port 80 to the 48 MHz data bus 58). After completion of a transfer, the AGP command generator 312 sends a FLUSH request to the interface device 70 to insure any remaining data buffered in the interface device 70 is sent to memory 72. Upon acknowledgement of a complete transfer, the controller 300 writes the event ID into the interrupt buffer 304. The CPU 74 is interrupted to indicate the availability of the data.

The service controller 306 arbitrates between requests for transfer and enables the requesting path to send the event ID and any other information associated with the transfer request to the controller 3000.

Referring to FIG. 2, the data transfer controller 68 performs arbitration and data buffering, data flow control, data reformatting or repacketizing, protocol and interface signal translation, and packet starting address generation. The data transfer controller 68 is a source of or provides ultrasound data to various components of the system 50. Preferably, the data transfer controller 68 time interleaves burst transfers of packets of ultrasound data between the memory 72 and any of the ultrasound data processing paths, such as the ultrasound acoustic data acquisition path 60, the video/audio acquisition path 62 and the video/audio reconstruction path 64.

The data transfer controller 68 buffers ultrasound data transferred to the memory 72 based on various requirements of the data processing system 52. Both the data transfer controller 68 and the interface device 70 include buffers. The interface device 70 queues or buffers data to minimize latency, maximize bandwidth and support concurrence of transfers on each port of the interface device 70. The buffers preferably include dedicated write buffers and read buffers, but other buffer structures, such as one buffer for both read and write operations, may be used. To maximize transfer efficiency, the data transfer controller 68 transfers only ultrasound data (PCI or control commands transfer, as specified by the AGP specification, are not supported, but may be in other embodiments). Other transfer schemes may be used.

Buffering is also performed in the paths interfacing to the ultrasound data bus 58.

The size of any buffer to prevent the loss of data is based on data path bandwidth and maximum transfer latency. For example, the sum of the ultrasound data bandwidth requirements of the ultrasound acoustic data acquisition path 60, the video/audio acquisition path 62, and the video/audio reconstruction path 64 is less than the sustainable bandwidth supported by the interface device 70 between the data port 80 and the memory port 76. The memory 72 bandwidth sustainable by the interface device 70 preferably includes time or bandwidth required for concurrent transfers between the CPU port 78 and the memory port 76, and the system port 82 and the memory port 76. Buffering by the interface device 70 allows for latency of any real-time transfer of ultrasound data while control or other data is transferred through the interface device 70 and allows more efficient burst transfers between ports. Buffering by the data transfer controller 68 allows for latency of data transfers on the data port 80 permits repackatizing and isolates clock domains between the data port 80 and the ultrasound data bus 58. Local buffers in the paths connected to the ultrasound data bus 58 absorb bus latency and the size of local buffers may be determined as follows:

$$\frac{\text{Minimum buffer}}{\text{size (bytes)}} = \frac{\text{local data rate}}{(\text{Mbytes/sec})} \times \frac{\text{transfer latency}}{(\mu\text{sec})}$$

Preferably, the maximum transfer latency is 100 $\mu$sec, but other latencies may be used.

When considering concurrent operation of all the ports of the interface device 70 and data transfers to the memory 72, the bandwidth of the memory port 76 may be the limiting factor and may require trade-offs between the bandwidth requirements for the CPU port 78, data port 80, and the system port 82. Increasing the bandwidth of the memory 72 through the use of higher clock rates, wider data widths or more efficient transfers permits higher concurrent bandwidths on the other ports of the interface device 70 for transfers to the memory 72.

Preferably, the data transfers between the data port 80 of the interface device 70 and memory 72 are non-coherent (i.e. cache memory on the CPU port of the interface 70 is not accessed or any cache status updated as part of the data transfer). Non-coherent transfers eliminate potential performance degradation resulting from coherency testing (snooping) of each transfer. Preferably, software is provided for maintaining the coherency between the cache memory and the memory 72 to ensure that valid data is used during data processing and placed in the memory 72 after data processing. Thus, the CPU 72 establishes coherency as part of its data processing operation. In alternative embodiments, the CPU 74 uses the memory 72 for processing the ultrasound image data without using the cache memory, or snooping may occur during transfers on the data port 80 to or from memory 72. Preferably, coherency between the cache memory of the CPU 74 and the memory 72 is maintained for transfers of data, such as control information, ultrasound data, and patient information, to or from the memory 72 through the system port 82, and to or from main memory 72 through the CPU port 78.

Various devices comprising sources of ultrasound data, such as in the ultrasound acoustic data acquisition path 60, the video/audio acquisition data path 62 and the video/audio reconstruction path 64, are described below as an example. Any device capable of providing the type of ultrasound data may be used. Likewise, any device capable of receiving appropriate control instructions may be used. The format of the data (image, audio, control or other) provided to or from the device is consistent with the format of the appropriate other devices of the system 50.

Figure 4:
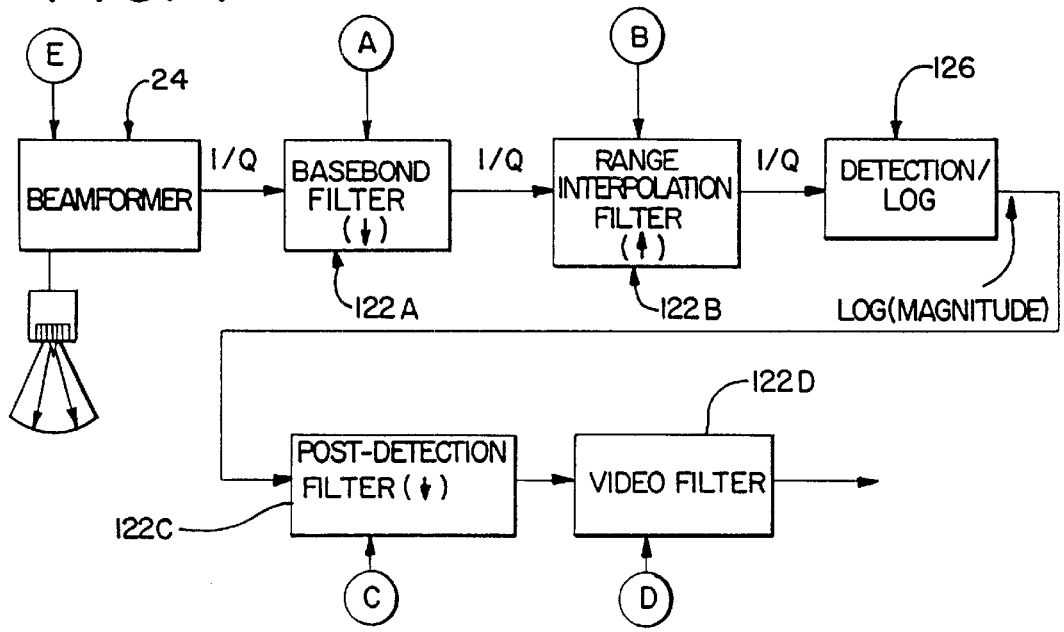
FIG. 4 is a block diagram of one embodiment of an ultrasound acoustic data acquisition path of FIG. 2.

One source of ultrasound data for processing is the ultrasound acoustic data acquisition path 60. Referring to FIG. 4, an ultrasound acoustic data acquisition path for B/M-mode is shown at 120. The acquisition data path 120 includes one or more filters 122A–D, a log compression and detection circuit 126. Additional components may be included. Any of the filters 122A–D and the log compression and detection circuit 126 may be implemented with a digital signal processor or other hardware. The acquisition data path 120 receives information from the beamformer 24, such as complex baseband ultrasound image data. The acquisition data path 120 performs analytic, detection and other post-detection processing to generate one or more of B-mode or M-mode information. The acquisition data path 120 may comprise the data path disclosed in U.S. application Ser. No. 08/760,083 for an Ultrasonic Diagnostic Imaging System With Programmable Acoustic Signal Processor, filed Dec. 4, 1996 ('the 083 application). See also U.S. Pat. Nos. 5,623, 930, 5,642,732, 5,285,788, 5,165,413, and 5,014,710. Preferably, the acquisition data path 120 is capable of generating detected B-mode data, M-mode data, color Doppler unfiltered energy, filtered energy, velocity and variance data and spectral Doppler data (derived waveform, spectrum and audio).

The processing carried out by the acquisition data path 120 and the beamformer 24 are connected to the system bus 56 for receiving control information from the CPU 74. The control information is either routed from the CPU port 78 to the system port 82 or from the memory 72 to the system port 82. The control information includes filter parameters, input controlling the selection of parameters (filter, Doppler or others), and other inputs controlling processing.

The control instructions preferably control the range grid for display. Complex baseband signals sampled on an initial range grid from the beamformer 24 are supplied as input data to a baseband filter 122A. In general, the baseband filter 122A performs harmonic (or fundamental) noise suppression filtering in the range dimension on the complex baseband signals from the beamformer 24, and provides selectable sampling rate decimation in range by a factor of L/M. Preferably, the bandwidth of the baseband filter 122A is adjusted as a function of the selected ratio L/M to band limit the signal prior to decimation and to prevent aliasing, as is well known in the art.

The baseband filter 122A supplies band limited and resampled complex baseband data to a range interpolation filter 122B. The range interpolation filter 122B performs up-sampling in range prior to nonlinear detection and log processing. The range filter 122B performs up-sampling by a factor of R/S. The decimation factor L/M and the interpolation factor R/S are preferably selected as a function of a number of parameters, including the size of the image to be displayed, the transmit center frequency, the number of samples to be displayed, and the number of beams. In this embodiment, decimation by the baseband filter 122A (L|M<1) is never employed in conjunction with range interpolation by the range interpolation filter 122B (R/S>1). In alternative embodiments, the baseband filter 122A and range filter 122B may be combined into a common block which implements both the L/M and the RIS resampling selections.

The output samples generated by the range interpolation filter 122B are supplied to a detection stage 126, which performs magnitude detection and log compression on each data sample. The data samples supplied by the range interpolation filter 122B are on an intermediate range grid, which is equal to the initial range grid of the beamformer stage 24 modified by the factor (L/M)×(R/S). The detection stage 126 output is supplied to a post-detection filter 122C. The post-detection filter 122C performs sample rate decimation by a factor of 1 (no decimation) or ½. When decimation by ½ is selected, filtering or band limiting of the magnitude samples is performed prior to decimation to a final range grid. This is done to substantially prevent aliasing.

The intermediate range grid on which data is supplied to the detection stage 126 is preferably sufficiently fine (sampled at a high enough rate) to prevent aliasing due to spectral broadening which occurs through the nonlinear processing operations performed in the detection stage 126. The range grid required prior to nonlinear processing to prevent aliasing will be dependent on the overall bandwidth of the signal from the beamformer stage 24 and the frequency response employed in the baseband filter 122A. In general, as the final range grid value increases as described below, it is preferable to employ an intermediate range grid that is finer than the final range grid (more highly over sampled) and then to band limit and decimate down to the final range grid after nonlinear processing in the detection stage 126, to preserve information content and to prevent aliasing artifacts. For smaller values of the final range grid, the final range grid may be fine enough to sufficiently over sample the signal prior to nonlinear processing, in this way avoiding the need for increased over-sampling prior to nonlinear processing and subsequent band limiting and decimation after nonlinear processing.

Output samples from the post-detection filter 122C are sampled on the final range grid, and are supplied to a video filter 122D. The video filter 122D performs final shaping of the spectrum of the signal prior to scan conversion and display. The video filter 122D is programmable, and may be set to pass-through mode where no filtering operation is performed, or may be employed to perform further band limiting or band peaking (edge enhancement) on the range data.

Other acquisition data paths 120 may be used, such as with different filter structures or processes, including post detection variable filtering. For example, the systems disclosed with respect to FIGS. 1, 17 or 18 of the '083 application or other systems may be used. Furthermore, different components may be used, such as analog or digital.

Referring to FIG. 2 and in the preferred embodiment, the ultrasound acoustic data acquisition path 60 provides processing for various modalities, and provides direct acquisition and transfer of beamformer acoustic data. B-mode and M-mode data output by the ultrasound acoustic data acquisition path 60 consists of 8 bit samples of magnitude detected and log compressed acoustic data. Spectral Doppler data output from the ultrasound acoustic data acquisition path 60 consists of 8 bit spectral magnitude (128 point per spectrum), 16 bit of each of forward and reverse (left and right) audio, and 16 bits for each (e.g. such as 4 waveforms) of the derived waveform data. Doppler Tissue and Color Doppler data output from the ultrasound acoustic data acquisition path 60 consists of 8 bits of each of unfiltered energy, energy, velocity (signed) and variance. Beamformer complex acoustic data (pre-detection) output from the ultrasound acoustic data acquisition path 60 consists of 16 bits of each of I and Q data. Data output from the ultrasound acoustic data acquisition path 60 is generally packed in 32 bit words and grouped in packets representing an acoustic line, group, or specific interval of time. In alternative embodiments, other data types, formatting, packing and grouping may be employed.

The output from the ultrasound acoustic data acquisition path 60 is stored in the memory 72. In alternative embodiments, additional data may be stored in the memory 72 from the ultrasound acoustic data acquisition path 60, such as transducer positional information, or any data received from the beamformer 24.

Another ultrasound data path or portion of a data path is the video/audio acquisition path 62. The video/audio acquisition path 62 receives digital video or audio data from the video/audio reconstruction path 64 and analog video/audio data from the analog video/audio device 54. Additional sources of digital or analog video/audio data may be provided. The video information generally comprises ultrasound image data. Compressed or uncompressed video data stored in the memory 72 is formatted as 8 bits for each color component. The video information may be in YUV 4:4:4, YUV 4:2:2, Y only, or RGB color spaces or any alternative color space and component sub-sampling. Preferably, YUV 4:2:2 data is stored in the memory 72 as two files, such as one file of progressive Y and a second file of U/V interleaved data. Alternatively, a four file format of Y and U/V component interleaved planes for even and odd field (such as for VCR playback) or other formats are used. The video/audio acquisition path 62 performs analog to digital and digital to analog conversion. Digital video or audio information is output to the ultrasound data bus 58 for storage in the memory 72 and any subsequent processing by the CPU 74. Data from the video/audio reconstruction path 64 is input to the video/audio acquisition data path 62 for analog video standards conversion and output to the analog video/audio device 54.

The video/audio acquisition path 62 preferably also performs real time video compression and decompression. The video/audio acquisition path 62 may perform fewer, additional or different functions. The video/audio acquisition path 62 preferably compresses and decompresses using the Joint Photographics Expert Group (JPEG) compression standard (ISO 10918 Draft International Standard) or other standards. Prior to compression, the video ultrasound data may be minified or scaled to further reduce the amount of information for storage. Any compressed video ultrasound data stored in the memory 72 may be transferred to the video/audio acquisition data path 62 over the ultrasound data bus 58 for decompression or transferred over the system bus 56 to an external peripheral. Decompressed ultrasound data is saved in the memory 72 and then transferred to the video/audio reconstruction data path 64 for reconstruction and output.

The video/audio acquisition path 62 preferably also supports static video frame capture of digital video data from the video/audio reconstruction path 64, and subsequent transfer to the memory 72. The CPU 74 may then compress the video data using either lossless or lossy compression algorithms. Compressed data stored in the memory 72 may be decompressed by the CPU 74.

Another ultrasound data path or portion of a data path is the video/audio reconstruction path 64. Referring to FIG. 5, the video/audio reconstruction path 64 comprises waveform and image reconstruction circuitry 140 and 142, waveform and image display plane memories 144 and 146, and combining circuitry 148. As another example, U.S. Pat. Nos. 5,563,810 and 5,479,926 discuss reconstruction processing and structures. The video/audio reconstruction path 64 receives text and graphics plane data, waveform data, and ultrasound data (decompressed video, B-mode acoustic, M-mode acoustic, color Doppler acoustic, spectral Doppler or other types of data) to be used in constructing an image for display. The ultrasound data is combined with the waveform data and the text and graphics plane data and output to a display 34, the video/audio acquisition path 62 or other outputs.

The image reconstruction circuitry 142 receives the ultrasound image data. The image reconstruction circuitry 142 comprises various processing stages for performing enhanced contrast resolution imaging, color Doppler frame interpolation, automatic area measurement processing, color mapping, or other processes. For example, see U.S. Pat. No. 5,479,926 to Ustuner et al. Other processes may include decompression or other operations optimally performed after bulk storage and prior to image reconstruction and display. The image reconstruction circuitry 142 performs scan conversion or spatial transformation and resampling operations to map data received on an acoustic grid or other grid to a display grid. For example, the processing disclosed in U.S. Pat. No. 5,563,810 for a Device And Method For Performing Acoustic Scan Conversion is used. The reconstructed ultrasound image data is stored in the image display plane memory 146.

The waveform data, including spectral Doppler derived waveform data and physiological waveform data is reconstructed or formatted for display by the waveform reconstruction circuitry 140. The reconstructed waveform information is stored in the waveform display plane memory 144.

Text and graphics plane data, such as non-scrolling data is passed through a queue 150 to the combining circuitry 148. Preferably, the text and graphics plane data is generated by the CPU 74 and stored in the memory 72. For example, the CPU 74 uses the ultrasound data or any other data, such as physiological data, to calculate quantities. The quantities are stored in the memory 72 as data or textual information, along with calipers or other graphic information. Multiple frames of text and graphics plane data are preferably stored in the memory 72 and selected by changing an address pointer.

Plane data, such as text and graphics plane data, is data stored uncombined with other types of data. For example, combined data is video data including text and image information. Text and graphics plane data is output to or within the video/audio reconstruction path 64 for combining with other types of data. Typically, plane data is output for combination at a rate corresponding to an update rate of the receiving device, such as the display 34. The text and graphics plane data is output from the memory 72 or another source at a rate that is substantially the same as an update or refresh rate of display 34. Due to the other potential bandwidth requirements of the memory port 76, the queue 150, such as a 1k×32 first-in, first-out buffer, absorbs any latency in receiving the text and graphics plane data. Thus, the memory 72 outputs the text and graphics plane data at substantially the same but varying rate as the refresh rate of the display 34. The first-in, first-out text queue 150 acts to output without variation the text and graphics plane data at substantially the same rate as the refresh rate of the display 34. Preferably, the text and graphics data is converted to RGB values with a look-up table prior to combination.

The text queue 150, the waveform display plane memory 144, and the image display plane memory 146 output data at substantially the refresh or update rate of the display 34 to the combiner 148. The combining circuitry generates composite ultrasound video data. The ultrasound video data is converted to analog and displayed on the monitor or display 34. The display 34 comprises a CRT or flat panel device.

The video/audio reconstruction data path 64 receives control plane data from the memory 72. Preferably, the control plane data comprises 4 bits/pixel for each black-and-white and color pixel, but other data formats may be used. The control plane data is stored in a 1K×32 FIFO buffer for subsequent use. The control plane data provides control information for the processing and combination of data, such as color or black-and-white look up table palette selection, identification of scrolling regions, strip or waveform identification, threshold map selection (programmable thresholds), black-and-white/color combining selections, image mask selection (clipping), and blanking background color (user selected). Preferably, the control plane data is transferred over the ultrasound data bus 58 and output from the memory 72 at a rate corresponding to the refresh rate of the display 34.

Spectral Doppler audio, microphone (or other external audio information), and physiological audio (phono physio) data is also transferred from the memory 72 or another source to the video/audio reconstruction data path 64. The various audio data is re-sampled and combined or mixed to generate a composite audio output. The audio information is output to the speakers 36, transferred to the memory 72 for storage, or output to another peripheral.

The system described above allows for flexible processing of ultrasound data and flexible control of processing. The CPU 74 controls the system 50 and performs ultrasound data processing. The memory 72 stores instruction code for the operation of the CPU 74, ultrasound data, control data, text and graphics data, and other data. The interface device 70 allows for efficient access between the CPU 74, the memory 72, various system data paths through the system port 82, and various ultrasound data paths hrough the data port 80.

II. Operation

Referring to FIG. 9, a flow chart of the operation of the CPU 74 (FIG. 2) is shown at 400. The CPU 74 first initializes the system as represented by block 402. For example, various system checks are performed, and components (e.g. PCI compliant devices connected to the system bus 56) are configured for operation. Further operation of the CPU 74 is preferably performed in a multi-tasking environment. The various operations or functions are time interleaved. For example, the processing associated with two or more of a peripheral operation block 404, a memory management processing block 406, a user interface and other control processing block 408, a data processing block 410, and an application processing block 412 is interleaved. Preferably, the amount of time dedicated to each operation is dynamically based on the type of operation, the time of any request for the operation, and any other priority information.

An example of the processing associated with each block 404, 406, 408, 410 and 412 is discussed below with reference to FIGS. 2 and 9. Other organizations of flow may be used, such as additional or fewer processing tasks. Furthermore, different, more or less processing may be performed for each block 404, 406, 408, 410 and 412.

Upon power up, the CPU 74 executes from a non-volatile memory, such as an EEPROM, containing initial boot code. The boot code loads additional code from disk or LAN into the memory 72 for the CPU 74 to execute. The CPU 74 accesses the memory 72 through the interface device 70. Pursuant to the instruction code data, the CPU 74 controls operation of various components of the system 50.

The CPU 74 configures the interface device 70 and the peripheral interfaces 66 to communicate with peripherals, such as the user interface 42 or the local area network 32 (block 402 of FIG. 9). Information from a peripheral device is transferred on the system bus 56 to the memory 72 through the system port 82 and memory port 76. Alternatively or additionally, the information is provided to the CPU 74. The information may include new instruction code and data transferred from disk or system 50 mode selection data from the user interface. For example, the user selects B-mode or other operating modality, specific processing options, or other system operating modes. Other data may be downloaded through the peripheral interface to the memory 72 (block 404 of FIG. 9).

For a user selected mode of operation, the CPU 74 provides control instructions to the beamformer 24, the ultrasound data acquisition path 60, the video/audio acquisition path 62, the video/audio reconstruction data path 64, any peripherals (e.g. physio module or analog video/audio device 54) or combinations thereof over the system bus 56 (blocks 404 and 408 of FIG. 9). The control information designates operating modality, scan format, scan region, focus, gain, other beamformer controls (e.g. imaging parameters) and other settings selected by the user or predefined for the mode of operation. Different types of control information may be used, such as filtering parameters, scaling parameters and other information usable by one or more of the various data paths. Predefined settings for a particular mode of operation are stored in the memory 72, and may be changed or loaded from various peripherals, such as the LAN 32, the removable media device 30, or the hard disk drive 28. The control instructions may be provided from the memory 72 to the system port 82. Likewise, interprocessor communications are stored in the memory 72 and then provided to appropriate processors.

The control instructions provided by the CPU 74 depend upon the type of ultrasound data processing selected by the user. For example, the user may select to acquire ultrasound data from the ultrasound acoustic data acquisition path 60, or the video/audio acquisition data path 62. For the ultrasound acoustic data acquisition path 60, the CPU 74 sends control and parameter information to initialize or otherwise configure the various components in the ultrasound acoustic data acquisition path 60 and the beamformer 24. For acquiring ultrasound data from the video/audio acquisition data path 62, the CPU 74 sends control and parameter information to initialize or otherwise configure the video/audio acquisition data path 62. For example, the video/audio acquisition data path 62 is configured to receive analog or digital video and audio information and to compress or decompress the information.

In preparation for transferring acquired ultrasound data over the ultrasound data bus 58 to the memory 72, the CPU 74 also initializes or configures the data transfer controller 68 (block 402 of FIG. 9). The CPU 74 dynamically manages the data transfer controller 68 during real time operation of the system. The data transfer controller 68 receives the CPU 74 control data from the system bus 56. The CPU 74 initializes the data transfer controller 78 for the type of transfer (i.e. read or write) and the starting logical address associated with the ultrasound data. The assigned event ID corresponds to the transfer type and the starting logical address of the allocated memory block. The event ID also identifies packet size, interrupts, routing and other control information.

The event ID is generated by the CPU 74 in response to a request from the beamformer 24 or another ultrasound data path. For example, the beamformer 24 requests space in the memory 72 for storage of acquired ultrasound data, such as B-mode acoustic line data. In the example of B-mode operation, the request is for memory space for one or more lines or frames of B-mode data. In other examples, the request may be for space for one or more frames of B-mode information, one or more frames of color Doppler information and/or lines, frames or other appropriate groupings of other data. The amount of data, the division of the data, such as in packets corresponding to a line or other set of information, and the number of packets within any grouping or set of information is programmed by the CPU 74. As used herein, a group or set of information includes one or more packets of information.

In response to the request, the CPU 74 allocates one or more memory sections, such as 4 kilobyte sections of the memory 72, to store the ultrasound data (block 406 of FIG. 9). The allocated memory comprises one or more physically continuous or discontinuous 4 kilobyte or other size memory sections. Based on the physical address of the segments within the memory 72, the CPU 74 generates a Graphics Address Remapping Table (GART) or other address table for use in logical to physical address translation. The CPU 74 assigns logically contiguous ultrasound data packets in allocated memory 72 to various physical memory sections and stores the assignment in the GART. Preferably, the table comprises a list of physical addresses indexed by logical addresses, but other table structures may be used. Preferably, only upper physical address bits are stored in the table and correspond to 4 kbyte sections. The upper sequential (logical) address bits are used to index the table, which provides the upper physical address bits that are concatenated with lower sequential bits to form the full physical address. For 256 Mbytes of ultrasound image data, the translation table preferably contains 64K entries, and a 256 kilobyte table. Other size tables may be used.

The event ID is provided to the beamformer 24 to acknowledge and respond to the request for the allocation of memory. Preferably, the event ID is a 10-bit field, allowing 1024 unique transfer events and allocated memory blocks to be concurrently used and managed by the CPU 74. Other size fields and numbers of transfer events may be used.

Based on the control information from the CPU 74 over the system bus 58, ultrasound data is acquired. For example, the ultrasound acoustic data acquisition path 60 obtains and processes ultrasound image information. When the processed ultrasound image information is ready for transfer to the memory 72, the ultrasound acoustic data acquisition path 60 generates a request for transfer to the data transfer controller 68. The request communicates a device identifier and the event ID to employ for generation of the logical address and control of the transfer operation.

In response to receiving the transfer request and event ID, the data transfer controller 68 transfers the ultrasound data over the ultrasound data bus 58. The data transfer controller 68 generates a starting address for each packet of data received from the ultrasound data bus 58 based on the transfer control parameters associated with the event ID. For B-mode and color Doppler mode ultrasound image data, the packet size is preferably associated with one acoustic line of data (e.g. 128–576 samples). For each successive packet associated with an event ID, the data transfer controller 68 computes the starting logical addresses. The packet associated with the last line of a frame or last packet for the event (multiple frames or less than one frame) preferably employs a unique event ID or passes a control bit to the data transfer controller 68 to signify the last transfer. This unique identification signifies completion of the transfer of ultrasound data associated with the event ID.

The interface device 70 receives the logically addressed ultrasound data from the data transfer controller 68 through the data port 80. The interface device 70 passes the ultrasound data to the memory 72 through the memory port 76. Preferably, the interface device 70 supports concurrent transfer of data between the CPU port 78 and the system port 82. Concurrent transfers from any two ports of the interface device 70 to other ports of the interface device 70 are also possible in alternative embodiments. The concurrent transfer of information through the interface device 70 reduces latency and improves data throughput.

In addition to concurrent routing as discussed above, the interface device 70 arbitrates and buffers data, such as ultrasound data or control data, destined for the same port of the interface device 70. For example, ultrasound data from the data port 80 is to be transferred to the memory port 76, and user interface or other data is to be transferred from the system port 82 to the memory port 76 at substantially the same time. The interface device 70 arbitrates by selecting data from either the data port 80 or system port 82 for transfer at a particular time. Concurrent transfers to the interface device 70 occur on both ports 80, 82, but then the interface device 70 arbitrates between the buffered data before writing to the memory 72. Information associated with the non-selected port, such as the system port 82, remains buffered. The buffered data is transferred when the memory port 76 is available. Preferably, the interface device 70 alternates between data from the data port 80 and the system port 82 for access to the memory port 76. On reads from the memory 72, arbitration occurs before the transfer, but alternatively, the interface device 70 reads ahead and locally buffers read data. The data is output from the buffer instead of accessing the memory port 76 to avoid arbitration. Arbitration between any two or more of the four ports of the interface device 70 for data transfers destined for any one of the ports for the interface device is possible.

In routing and transferring ultrasound data to the memory port 76 from the data port 80 of the interface device 70, the interface device 70 translates the logically addressed ultrasound image data addresses to physical memory addresses. Other addressing schemes and translation schemes may be used, such as providing translation with the data transfer controller 68. The translation scheme allows the allocation of large logically contiguous address ranges in physically discontiguous memory segments and permits the memory 72 to be efficiently utilized even where the process of allocation and deallocation of memory segments creates physically fragmented memory space. Preferably, the same logical to physical address translation is performed for any transfer of ultrasound data to or from the memory 72. The CPU 74, the data transfer controller 68 and the system bus 56 all access the same ultrasound data (data within the address range assigned to the data port 80) in the memory 72 using the same logical address scheme.

To translate the logical addresses to the physical addresses, the interface device 70 uses the GART or other table generated by the CPU 74. Preferably, the GART is stored in the memory 72 and contains address pointers for each 4 Kbyte physical memory segment. Preferably, the interface device 70 includes a memory for caching at least the last two or more translation table address pointers used (physical addresses). By caching a portion of the table, requiring access to the memory 72 for each address translation may be avoided. In alternative embodiments, the interface device 70 stores the entire table. As yet another alternative embodiment, physical address locations are assigned to the ultrasound data by the data transfer controller 68. Furthermore, a separate memory for storing the translation table may be used.

After a physical address is associated with each packet of ultrasound data, the interface device 70 transfers the ultrasound data to the memory 72 in a burst fashion. Other transfer techniques may be used. When performing transfers to or from the memory 72, the interface device 70 activates a bank of the memory and selects a particular page of one or more memory components. Successive transfers to or from the same page preferably occur on each successive clock cycle, when memory is comprised of SDRAM, to maximize the data transfer rate. For a memory port 76 employing a 64 bit wide data path and a 64 megahertz clock, transferring data on every clock yields a maximum data transfer bandwidth of 512 Mbytes/sec. Other data widths and clock speeds may be used. Interleaving burst transfers of ultrasound data to different pages in the same memory components requires additional overhead and reduces the effective bandwidth of the memory 72. By providing multiple blocks, each with multiple banks, in the memory 72 and transferring to a previously selected page, interleaving of burst transfers in different banks occurs with reduced overhead. Other interleaving techniques may be used.

Storing ultrasound image data in a large buffer, such as the memory 72, permits ultrasound image data acquisition, ultrasound image data processing by the CPU 74, and reconstruction processing to be decoupled, allowing disparate acquisition, processing and output data rates to be used.

Once the transfer of the ultrasound data to the data transfer controller 68 and the memory 72 is complete, the data transfer controller 68 generates an interrupt to the CPU indicating completion. In response to the interrupt, the CPU 74 performs ultrasound image data processing or otherwise makes the ultrasound image data in the memory 72 available for processing, such as reconstruction and display processing. The ultrasound image data is altered or further processed by the CPU 74 or provided directly to a video/audio acquisition data path 62 or the video/audio reconstruction data path 64. Alternatively, the ultrasound image data is transferred across the system bus 56 to one or more peripherals. Preferably, the CPU 74 performs additional processing on the ultrasound image data stored in the memory 72. This additional processing is done in real time or substantially concurrently with the acquisition or output of ultrasound image data. Alternatively, the CPU 74 processes the stored ultrasound image information not in real time.

The CPU 74 obtains the ultrasound image data from the memory 72 through the interface device 70. As discussed above, the CPU 74 generates logical addresses to acquire ultrasound image data stored from the data port 80. The interface device 70 translates the logical addresses to physical memory addresses. The ultrasound image data from the memory 72 is transferred to the CPU 74 for processing.

The CPU 74 spatially filters (e.g. 3 tap m-mode range video filtering or azimuthal filtering), temporally filters (e.g. single tap adaptive or recursive persistence), weights, applies a threshold to, or selects particular parameters of the ultrasound image data (block 410 of FIG. 9). The CPU 74 may also perform combinations of these and other processes 25, such as depth gain compensation, compression scaling, edge enhancement, noise and speckle filtering, peak map/ frame average processing, energy weighting of velocity, and non-real time compression and decompression of video data. The CPU 74 may generate or recover encoded information, such as format, color palettes, or other information for obtaining measurements from image data, for or from blanking gaps in VCR or video data. For depth gain compensation, background noise vectors are stored in the memory 72, and the CPU 74 inverts and smooths the vectors to determine the compensation. Other processes, such as performed by the ultrasound data acquisition path 60, the video/audio acquisition path 62 or the video/audio reconstruction path 64, may be performed by the CPU 74. Preferably, only lossless compression and decompression is performed, but lossy compression and decompression on static or real time images may be used. Additionally, any of the various processes performed by the CPU 74 may be performed in other ultrasound data paths.

Preferably, the CPU 74 uses a single instruction to operate on multiple pieces of data concurrently. This process is repeated for one or more instructions. With the preferred single instruction multiple data processor, 8 byte operands are processed in a single clock cycle at a 350 MHz clock rate. Some instructions operate at this level, but others operate on 4 word or 2 double word operands.

Depending on the amount of data processing and other bandwidth uses of the CPU 74, the data processing may be constrained under certain operating conditions, such as performing noise and speckle filtering on color Doppler data only when the flow sample count is greater than a required minimum. Changing the frame display rate may also limit or broaden the amount of data processing performed by the CPU 74. The attached Section A demonstrates code for temporally persisting B-mode data. The code is designed to test the amount of time a Pentium MMX processor uses to persist B-mode data. For implementation on the system 50, additional or different code may be used.

For static or non-real time compression by the CPU 74, NTSC 640×480 or PAL 786×576 full screen compression using DICOM (Packbits) or other lossless schemes may be used. For static compression, separate compressed data segments for each component are generated by the CPU 74. For RGB or YUV color spaces, three progressive files are generated.

For static or non-real time decompression by the CPU 74, RGB 4:4:4, YUV 4:4:4, or 4:0:0 (monochrome) data at a preferable pixel grid size of 768×576 or less is decompressed based on the compression schemes discussed above. The compressed data is either planar (separate scan segments for each component within the frame) or component interleaved (single scan segment with components interleaved). Preferably, the decompressed data is planar.

In addition to any processing of the ultrasound data, the CPU 74 generates text and graphics for display with the ultrasound image data (block 412 of FIG. 9). The text or graphics information is non-scrolling information, such as input selection information displayed to the user, patient information, calculated quantities and other text. The text and graphics information is stored in the memory 72 as text and graphics plane data. The CPU 74 also generates control plane data. The control plane data is stored in the memory 72.

In alternative embodiments, the CPU 74 performs other ultrasound data processing tasks. For example, the CPU 74 generates three-dimensional image constructions or representations. The CPU 74 obtains ultrasound image information in a video or acoustic format and manipulates the information to generate a three-dimensional representation. For example, the CPU 74 processes ultrasound image data from the beamformer 24 (e.g. I and Q values or detected data) to generate transducer positional information. This process is discussed in U.S. Pat. No. 5,944,666, for an Ultrasonic Method for Imaging Blood Flow. As the three-dimensional representation or other data is generated by the CPU 74, the ultrasound data is stored in the memory 72. The ultrasound image data representing the three-dimensional construction or viewing planes associated with the three-dimensional reconstruction are stored in the memory 72 or output via the ultrasound data bus 58 for display.

For further discussion of the data processes performed by the CPU 74, see the attached Section D. In Section D, the CPU 74 is referred to as the Main Processor (MP) and the memory 72 is referred to as the main memory.

After storage in the memory 72, the ultrasound image data and other data is read out of the memory 72 for further processing, transfer through the peripheral interfaces 66, or transfer to other ultrasound data paths. Any of the ultrasound image or audio data stored in the memory 72, such as associated with different amounts of processing by ultrasound image data paths (including the CPU 74), is provided for display, further processing, or export. For example, the ultrasound image data provided by the video/audio acquisition path 62 or any other ultrasound image data path may be transferred from the memory 72 over the system bus 56 to any of various peripherals.

After one or more frames of ultrasound image data are ready for display, the CPU 74 communicates the availability to the video/audio reconstruction path 64 (block 408 of FIG. 9). The CPU 74 identifies the frame of data with the appropriate event ID, programs interface device 70 with the GART to obtain the ultrasound image data from the memory 72, and initializes the data transfer controller 68 for the type of transfer and starting logical address. The CPU 74 enables the video/audio reconstruction path 64, which generates a request for transfer of ultrasound image data. The request communicates the event ID to the data transfer controller 68. In response to the request, the data transfer controller 68 transfers the ultrasound image data from the memory 72 to the ultrasound data bus 58. Preferably, the image data is aligned on an acoustic or raster grid, but other grids may be used. Other information, such as text and graphics, control plane and waveform information is also transferred over the ultrasound data bus 58 to the video/audio reconstruction path 64. The video/audio reconstruction path 64 generates an image for the display 34 by combining the various display information, and generates audio by combining the various audio information.

As an alternative to acquiring ultrasound image data from the ultrasound acoustic data acquisition path 60 or outputting ultrasound image data to the video/audio reconstruction path 64, ultrasound image data is acquired or provided to the video/audio acquisition data path 62 or the peripheral interfaces 66. The transfers and processing of the ultrasound data discussed above are performed in the same or a similar manner.

Ultrasound data from two ore more different data paths, such as the ultrasound image acquisition path 60 and the video/audio acquisition data path 62 may occur substantially simultaneously. In this situation, the data transfer controller 68 arbitrates between requests for transfer and time interleaves ultrasound data packets on the data transfer bus 58 for transfer to or from the memory 72.

In a preferred embodiment, the transfers of ultrasound data over the ultrasound data bus 58 are managed by the CPU 74. Additionally, transfers of physio, or any other type of data stored in the memory 72 and transferred over the system bus 56 are managed by the CPU 74. The CPU 74 also manages the memory 72, including allocation and deallocation, assignment of event identifiers, GART loading, and data transfer controller 68 initialization and address generator table loading. The CPU 74 also dynamically directs the video/audio reconstruction data path 64 by identifying ultrasound data in the memory 72 for reconstruction. The packet sizes associated with any of the data, such as ultrasound data, audio data, patient information, text information, waveform information, control instructions may vary.

While the invention has been described above by reference to various embodiments, it would be understood that many changes and modifications can be made without departing from the scope of the invention. For example, an interface device 70 may have more or fewer ports. Other specifications and protocols may be used. More or less control and/or ultrasound image data processing may be performed by the CPU 74. Access to the memory may be provided without the interface device 70, such as through a memory port connected directly to various components.

It is therefore intended that the foregoing detailed description be understood as an illustration of the presently preferred embodiments of the invention, and not as a definition of the invention. It is only the following claims including all equivalents, that are intended to define the scope of this invention.

What is claimed is:

1. A method for operating an ultrasound system, the method comprising the steps of:

(a) providing user input to a processor;

(b) controlling operation of the ultrasound system with the processor;

(c) providing ultrasound image data in response to at least one control instruction from the processor;

(d) storing in a memory the ultrasound image data;

(e) processing the ultrasound image data with the processor; and (f) storing in the memory the processed ultrasound image data.

2. The method of claim 1 wherein the step (e) comprises processing selected from the group consisting of: temporal filtering, spatial filtering, thresholding, weighting and combinations thereof.

3. The method of claim 1 further comprising the step (g) of decompressing with the processor compressed ultrasound image data.

4. The method of claim 1 further comprising the step (g) of compressing the ultrasound image data.

5. The method of claim 1 further comprising the step (g) of constructing with the processor a three-dimensional representation.

6. The method of claim 1 further comprising the step (g) of providing system component control instructions selected from the group of: user interface control, a communications interface control, a data transfer bus controller control, an interface device control, a physical address generator control, a beamformer control, an ultrasound image data path control, a physio module control, a filter control, a digital signal processor control, a multiplexer control, a scan converter control, a peripheral control and combinations thereof.

7. The method of claim 1 wherein the step (c) comprises processing the ultrasound image data with a programmable single instruction multiple data processor.

8. The method of claim 1 further comprising the step of allocating memory with the processor.

9. The method of claim 8 further comprising the steps of:
generating a table of physical addresses indexed by logical addresses associated with the memory; and
storing the table in the memory.

10. The method of claim 1 wherein the step (e) comprises directly accessing the ultrasound image data from the memory.

11. The method of claim 1 further comprising the step of storing instruction code data in the memory, the processor responsive to the instruction code data.

12. The method of claim 1 wherein step (e) comprises the step of accessing the ultrasound image data through an interface device, the interface device operatively connected to the processor and a data bus.

13. The method of claim 1 wherein step (a) or (b), respectively comprises the step (i) of providing control instructions selected from the group consisting of: beamformer control, detector control, filter control, digital signal processor control, multiplexer control, and combinations thereof.

14. The method of claim 13 wherein the step (i) comprises providing initializing control data.

15. The method of claim 1 wherein the steps (b) and (e), respectively, comprise the steps of:
(i) providing with one of two symmetric processors control instructions; and
(ii) processing with the one of the two symmetric processors the ultrasound image data.

16. The method of 15 wherein the steps (i) and (ii) comprise:
(a) providing with a second of the two symmetric processor control instructions; and
(c) processing with the second of the two symmetric processors the ultrasound image data.

17. The method of claim 1 wherein the steps (b) and (e) respectively, comprise the steps of:
(i) providing with a first of two symmetric processors control instructions; and
(ii) processing with a second of the two symmetric processors the ultrasound its image data.

18. The method of claim 15 further comprising the step of providing the two symmetric processors with input/output symmetry.

19. The method of claim 18 further comprising the step of providing the two symmetric processors with memory symmetry.

20. The method of claim 1 further comprising the step of calculating with the processor a quantity from the ultrasound image data.

21. An ultrasound system for generating image data, the system comprising:
a data bus;
a system bus for providing user input;
a processor for receiving the user input, for controlling operation of the ultrasound system and for processing ultrasound image data from the data bus; and
a memory for storing the processed ultrasound image information from the processor.

22. The system of claim 21 wherein the processor is operable to perform processing selected from the group consisting of: temporal filtering, spatial filtering, thresholding, weighting and combinations thereof.

23. The system of claim 21 further comprising a display comprising an ultrasound image responsive to the processed ultrasound image data.

24. The system of claim 21 wherein the processor for controlling operation comprises a processor for providing control instructions selected from the group consisting of: user interface instructions, communications interface instructions, data transfer controller instructions, scan converter instructions, peripheral instructions, interface device instructions, physical address generator instructions, beamformer instructions, ultrasound image data path instructions, physio module instructions, filter instructions, digital signal processor instructions, multiplexer instructions, and combinations thereof.

25. The system of claim 21 wherein the processor comprises a programmable single instruction multiple data capable processor.

26. The system of claim 25 wherein the processor comprises a multi-media extension processor.

27. The system of claim 21 wherein the memory stores a table of physical memory addresses indexed by logical memory addresses.

28. The system of claim 21 wherein the memory stores instruction code data and the processor is responsive to the instruction code data.

29. The system of claim 21 further comprising an interface device operatively connected to the processor, the data bus and the system bus.

30. The system of claim 29 wherein the interface device provides direct access to the memory by the processor, the data bus and the system bus.

31. The system of claim 21 wherein processor comprises two input/output symmetric processors.

32. The system of claim 21 wherein the processor comprises two memory symmetric processors.

33. An ultrasound system with data storage capabilities, the system comprising:
a memory comprising at least one memory component for storing ultrasound image data and processor instruction code data;
a memory access device operatively connected to the memory, the access device for controlling the transfer of ultrasound image data from or to the memory; and
a processor operatively connected to the access device, the processor operable to execute at least some of the processor instruction code data.

34. The system of claim 33 wherein the memory stores the ultrasound image data and processed ultrasound image data from the processor.

35. The system of claim 33 wherein the memory access device provides direct access to the memory by the processor.

36. The system of claim 33 wherein:
the memory comprises a plurality of physically addressed memory components;
the ultrasound data is logically addressed; and
the memory access device stores ultrasound image data in the physically addressed memory components in response to the logical addresses.

37. The system of claim 33 wherein the memory access device provides access to the memory by the processor and a source of the ultrasound data with a same logical address scheme.

38. The system of claim 37 wherein the memory access device provides direct access by the processor and the source to the memory.

39. The system of claim 33 wherein the memory access device comprises a quad port interface device.

40. The system of claim 37 wherein the memory is operable to store a table of addresses.

41. The system of claim 33 wherein the processor comprises a single instruction multiple data system processor.

42. The system of claim 33 wherein the memory is operable to store text plane information.

43. The system of claim 33 wherein the ultrasound image data comprises image data selected from the group consisting of: acoustic line data, video data, B-mode data, M-mode data processed image data, spectral Doppler data, color Doppler data, compressed image data, uncompressed image data, beamformer output data, processed beamformer acoustic data, and combinations thereof.

44. The system of claim 33 wherein the memory is further operable to store data selected from the group consisting of: audio data, ECG data, pressure data, respiration data, DC-A data, DC-B data, DC-C data, DC-D data, communication data, interface data, interprocessor communication data, waveform data, quantity data, and combinations thereof.

45. The system of claim 33 wherein the processor is operable to provide control signals in response to the processor instruction code data.

46. A method for storing data in an ultrasound system, the method comprising the steps of:
  (a) storing ultrasound image data and processor instruction code data in a memory comprising at least one memory component;
  (b) controlling with an access device the transfer of data from or to a memory; and
  (c) executing with a processor the processor instruction code data.

47. The method of claim 46 wherein the step (b) comprises providing direct access to the memory by the processor.

48. The method of claim 46 further comprising the step (d) of storing in the memory processed ultrasound image data from the processor.

49. The method of claim 46 wherein the memory comprises a plurality of physically addressed memory components and the ultrasound image data is logically addressed; and wherein the step (b) comprises storing the ultrasound data in the physically addressed memory components in response to the logical addresses.

50. The method of claim 46 wherein the step (b) comprises providing direct access to the memory by the processor and a source of the ultrasound image data with a same logical address scheme.

51. The method of claim 49 further comprising the step (d) of storing a table of addresses in the memory.

52. The method of claim 46 further comprising the step (d) of storing text plane information in the memory.

53. The method of claim 46 wherein the step (a) comprises storing ultrasound image data selected from the group consisting of: acoustic line data, video data, B-mode data, M-mode data, processed image data, spectral Doppler data, color Doppler data, compressed image data, uncompressed image data, and combinations thereof.

54. The method of claim 46 further comprising the step (d) of storing in the memory data selected from the group consisting of: audio data, ECG data, pressure data, respiration data, DC-A data, DC-B data, DC-C data, DC-D data, communication data, interface data, interprocessor communication data, waveform data, quantity data, and combinations thereof.

55. The method of claim 46 further comprising the step (d) of providing with the processor control signals in response to the processor instruction code data.

* * * * *